US008669078B2

(12) United States Patent
Pan et al.

(10) Patent No.: US 8,669,078 B2
(45) Date of Patent: Mar. 11, 2014

(54) AMMONIA-SPECIFIC 5'-XMP AMINASE MUTANT

(75) Inventors: Jae-Gu Pan, Chungeheongnam-do (KR); Heung-Chae Jung, Daejeon (KR); Eui-Joong Kim, Daejeon (KR); Han-Seung Lee, Daejeon (KR); Young Hoon Park, Gyeonggi-do (KR); Hyoung Suk Kim, Gyeonggi-do (KR); Jong-Kwon Han, Gyeonggi-do (KR); Jin Nam Lee, Gyeonggi-do (KR); Ki-Hoon Oh, Seoul (KR); Jeong Hwan Kim, Seoul (KR); Yoon-Suk Oh, Gyeonggi-do (KR); Jae Ick Sim, Gyeonggi-do (KR); Kuk-Ki Hong, Seoul (KR); Kyung Oh Choi, Busan (KR); Hyun Soo Kim, Gyeonggi-do (KR); Min-Ji Baek, Seoul (KR); Tae Sun Kang, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 989 days.

(21) Appl. No.: 12/097,104

(22) PCT Filed: Dec. 14, 2006

(86) PCT No.: PCT/KR2006/005475
§ 371 (c)(1),
(2), (4) Date: Aug. 11, 2008

(87) PCT Pub. No.: WO2007/069861
PCT Pub. Date: Jun. 21, 2007

(65) Prior Publication Data
US 2008/0318278 A1    Dec. 25, 2008

(30) Foreign Application Priority Data

Dec. 14, 2005    (KR) .................. 10-2005-0123529

(51) Int. Cl.
*C12P 19/40*    (2006.01)
*C12P 21/06*    (2006.01)
*C12N 15/00*    (2006.01)
*C07H 21/02*    (2006.01)

(52) U.S. Cl.
USPC .......... 435/88; 435/440; 435/320.1; 536/23.1

(58) Field of Classification Search
None
See application file for complete search history.

(56) References Cited

U.S. PATENT DOCUMENTS 6,210,951 B1    4/2001    Kawasaki et al.

FOREIGN PATENT DOCUMENTS

| KR | 2000/040840 A | 7/2000 |
|---|---|---|
| KR | 2006/0068505 A | 6/2006 |
| WO | 2006/065076 A1 | 6/2006 |

OTHER PUBLICATIONS

Massiere et al., Cell. Mol. Life Sci. 54, 205-222, 1998.*
Paluh, et al., "Study of Anthranilate Synthase Function by Replacement of Cysteine. 84 Using Site-directed Mutagenesis*.", the Journal of Biological Chemistry, 260(3):1889-1894, 1985.
NCBI GenBank Accession No. AAC75560 GMP synthetase (glutamine aminotransferase) [*Escherichia coli* str. K-12 substr. MG1655], Dec. 1, 2000.
Fujio, et al., "High Level Expression of XMP Aminase in *Escherichia coli* and Its Application for the Industrial Production of 5'-Guanylic Acid.", Biosci. Biotechnol. Biochem., 61(5):840-845, 1996.
Patel, et al., "Xanthosine-5'-phosphate amidotransferase from *Escherichia coli*.", J. Biol Chern., 250(7):2609-2613, 1975.
Extended European Search Report, for European Application No. 06835210.3, dated Mar. 25, 2011, 11 pages.
Hirst et al., "Human GMP Synthetase—Protein Purification, Cloning, and Functional Expression of cDNA," *The Journal of Biological Chemistry* 269(38):23830-23837, 1994.
Mehra et al., "Dual Control of the *gua* Operon of *Escherichia coli* K 12 by Adenine and Guanine Nucleotides," *Journal of General Microbiology* 123:27-37, 1981.
Nagahara et al., "Crystallization of XMP aminase and Crystallographic Review thereof," *The Chemical Society of Japan, 63rd Annual Spring Meeting Program* 2:1351, Abstract No. 1B518, 1992. (with English Translation).
Japanese Office Action, for Japanese Application No. 2008-545497, dated May 10, 2011, 4 pages.
Patton et al., "Production of Intein-tagged GMP Synthetase Mutant Proteins," *The Journal of the Pennsylvania Academy of Science, The Academy*, Harrisburg, US 77(No. Abstract and Index Issue):145, 2004. (XP009146027).
Tesmer et al., "The crystal structure of GMP synthetase reveals a novel catalytic triad and is a structural paradigm for two enzyme families," *Nature Structural Biology* 3(1):74-86, 1996.

\* cited by examiner

*Primary Examiner* — Nancy T Vogel
(74) *Attorney, Agent, or Firm* — Seed IP Law Group PLLC

(57) ABSTRACT

Disclosed herein are ammonia-specific 5'-XMP aminase mutants and a method for preparing the same. A mutation is introduced into the active site of glutamine-dependent catalysis in 5'-XMP aminase. The resulting 5'-XMP aminase mutant is devoid of the glutamine-dependent activity and specifically reacts with external ammonia in converting 5'-XMP into 5'-GMP. Thus, the ammonia-specific 5'-XMP aminase mutant is stabler within cells compared to the wild type, and can be useful in the industrial conversion of 5'-XMP into 5'-GMP.

8 Claims, 11 Drawing Sheets

AMMONIA-SPECIFIC 5'-XMP AMINASE MUTANT

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is 200187_405USPC_SEQUENCE_LISTING_txt. The text file is 118 KB, was created on Jul. 19, 2013, and is being submitted electronically via EFS-Web.

TECHNICAL FIELD

The present invention relates, in general, to a method of preparing a 5'-xanthylic acid (XMP) aminase mutant having enhanced activity, a 5'-XMP aminase mutant prepared according to the method, and a method for producing 5'-guanylic acid (GMP) at enhanced efficiency and, more particularly, to a method of preparing a 5'-XMP aminase mutant specifically reactive to ammonia, an ammonia-specific 5'-XMP aminase mutant prepared according to the method, and a method of producing 5'-GMP at high yield using the ammonia-specific 5'-XMP aminase mutant.

BACKGROUND ART

5'-Guanylic acid (GMP) rivals 5'-inosinic acid (IMP) as the most widely used flavor enhancer. 5'-GMP is one of the substances responsible for the taste of mushrooms. On its own, 5'-GMP does not have much taste, but its effect is noticeable when used in combination with monosodium l-glutamate (MSG). 5'-GMP creates a synergistic flavor-enhancing effect in combination with 5'-IMP.

Several methods are known for producing 5'-GMP, including: (1) the extraction of RNA from yeast and the enzymatic digestion thereof, (2) microbial fermentation for the direct production thereof, (3) microbial fermentation for forming guanosine, followed by the chemical phosphorylation of guanosine, (4) microbial fermentation for forming guanosine, followed by microbial phosphorylation of guanosine, (5) microbial fermentation for the production of 5'-XMP, followed by the conversion of 5'-XMP to 5'-GMP using *Corynebacterium* spp, or (6) microbial fermentation for the production of 5'-XMP, followed by the conversion of 5'-XMP to 5'-GMP by *E. coli*. Of these methods, Method (1) has problems related to material supply and economy, and Method (2) suffers from the disadvantage of having a low production yield because cell membranes are impermeable to 5'-GMP. For these reasons, the other methods are typically applied in industry.

In vivo, for the conversion of 5'-XMP to 5'-GMP, as in the case of Methods (5) and (6), 5'-XMP aminase is responsible, which catalyses the following reactions (Pantel et al. (1975), J. Biol. Sci., 250(7), 2609-2613).

5'-XMP aminase is a member of the glutamine amidotransferase superfamily. Glutamine amidotransferases hydrolyze glutamine at the gamma-amide group to generate ammonia. The resulting free ammonia is assimilated into amino acids, nucleotides, sugars, coenzymes, and the like through polymerization reactions. Glutamine amidotransferases have many various target substances, but the method by which glutamine is hydrolyzed to form ammonia has been well conserved during evolution. Glutamine amidotransferases have been divided into two subfamilies: class I and class II. The class I enzymes includes anthranilate synthase, carbamoyl phosphate synthetase, CTP synthetase, formylglycinamidine synthetase, 5'-xanthylic acid aminase, imidazole glycerol phosphate synthase, aminodeoxychorismate synthase, and p-aminobenzoate synthase. All of these enzymes use, in addition to glutamine, external ammonia as an amine donor (Cell Mol. Life Sci. 54, 205-222, 1998). Unlike how ammonia, free from glutamine, is transferred to a substrate, the external ammonia is considered to directly transfer to transferase.

In the context of protein structure, 5'-XMP aminase can be separated into two well-defined domains: one having glutaminase activity responsible for catalytic hydrolysis of glutamine and the other domain having transferase activity (Nat. Str. Biol. 3(1), 74-86, 1996). The N-terminal domain with glutaminase activity is structurally similar to carbamyl phosphate synthetase, which has been well studied. The glutaminase activity is mainly achieved by a catalytic triad of cysteine, histidine and glutamate residues, which is similar to the catalytic mechanism of cysteine protease (Cell Mol. Life Sci. 54, 205-222, 1998). Particularly in *E. coli*, cysteine 86, histidine 181 and glutamic acid 183 form a catalytic triad. In the enzymatic mechanism of glutaminase, the catalytic cysteine residue forms a gamma-glutamyl thioester bond with glutamine, with the histidine serving as a base for the hydrolysis of glutamine into glutamic acid and ammonia (Fukuyama et al. Biochemistry 3, 1448-1492, 1964; von der Saal et al. Biochemistry 24, 5343-5350, 1985). Through a channel formed in the enzyme, this ammonia participates in the conversion of 5'-xanthylic acid to 5'-guanylic acid (Raushel et al. Biochemistry, 38(25), 7891-7899, 1999).

XMP aminase-catalysed conversion of 5'-XMP to 5'-GMP using ammonia shows the same mechanism as that of the reaction using L-glutamine, but is subtly different in properties. 5'-XMP aminase, although optimal at pH 8.3 for both substrates, exhibits two or more times as much catalytic activity for L-glutamine as for ammonia (Pantel et al. (1975), J. Biol. Sci., 250(7), 2609-2613). The difference increases as the reaction pH approaches neutral, which implies that 5'-XMP aminase does not employ a solution phase of ammonia ($NH_3$), but takes advantage of L-glutamine in the conversion of 5'-XMP into 5'-GMP in vivo.

When treated with the cysteine-reactive sulfhydryl reagent Iodoacetamide or with the glutamine derivative chloroketone or acivicin, the activity of 5'-XMP aminase decreases with

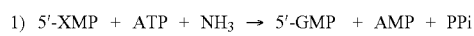

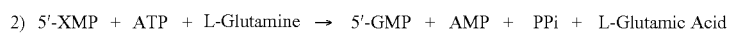

L-glutamine, but remains unchanged with ammonia, indicating that the cysteine residue at the active site of the glutaminase is essential for the glutamine-dependent activity of 5'-XMP aminase, but not for the ammonia-dependent activity of 5'-XMP aminase (Zalkin and Truitt, J. Biol. Sci. 252(15), 5431-5436, 1977; Massiere and Badet-Denisot, Cell Mol. Life. Sci. 54, 205-222, 1998).

In the case of anthranilate synthase, which belongs to the same class as 5'-XMP aminase, it is reported that the replacement of the conserved cysteine residue with glycine abolishes the glutamine-dependent anthranilate synthase activity but not the $NH_3$-dependent activity of the enzyme (Paluh et al., J. Biol. Chem. 260, 1889-8601, 1985). Also, when the conserved cysteine residue of para-aminobenzoate synthase is replaced by serine, the production of the γ-glutamyl thioester adduct is attenuated, which leads to a decrease in the production of aminodeoxychorismate (Roux et al., Biochemistry, 32, 3763-3768, 1993). As for carbamoyl phosphate synthetase, its glutamine-dependent activity also disappears when the conserved cysteine residue is replaced with serine or glycine (Rubino et al., J. Biol. Chem., 261, 11320-11327, 1986).

Typically, since native enzymes have evolved to have activity suitable for cells, they often exhibit properties unsuitable for industrial applications due to their low activity. To overcome this problem, gene cloning of an enzyme of interest and the overexpression thereof have typically been studied in the art. In practice, an 5'-XMP aminase gene (guaA) was successfully isolated from wild-type *Escherichia coli* and cloned into an inducible expression plasmid which can be applied for the production of 5'-GMP from 5'-XMP (Biosci. Biotech. Biochem. 61(5), 840-845, 1997).

Another method of increasing protein expression of wild-type bacteria using drug resistance is described in Korean Pat. Laid-open Publication No. 2000-0040840. In this publication, a mutant strain having enhanced activity of 5'-XMP aminase, which is prepared by imparting decoyinine resistance to a wild-type *Escherichia coli* strain, is provided for increasing the expression of a gene of interest.

Inducible expression vectors for general use require expensive expression inducers such as IPTG, and are thus not suitable for industrial applications involving protein production on a large scale. A constitutive expression system arises as a solution to this problem. A great number of constitutive expression systems have been reported. In particular, a novel constitutive expression promoter was developed for *Corynebacterium ammoniagenes* known to be suitable for the fermentative production of nucleic acids (Korean Pat. Application No. 2004-107215). The constitutive expression systems are useful because they sustain the expression of an introduced protein for a cultivation period of host cells without the use of an expression inducer. However, when the overexpression of an introduced protein affects the growth of host cells, the cells stop growing, or a vector introduced into the cells is removed, resulting in low expression efficiency. The same results have been reported for 5'-XMP aminase (Biosci. Biotech. Biochem. 61(5), 840-845, 1997).

The growth halt or the vector removal in the constitutive expression system of 5'-XMP aminase is, in the opinion of the present inventors, attributable to the cytotoxicity of the constitutively overexpressed product. As a solution for circumventing this problem, the present inventors suppressed the glutaminase activity of 5'-XMP. As mentioned above, since 5'-XMP aminase utilizes L-glutamine to convert 5'-XMP into 5'-GMP within cells, an L-glutaminase activity-suppressed 5'-XMP aminase mutant has decreased activity in, and thus low toxicity to, cells. Furthermore, the 5'-XMP aminase mutant retains ammonia-dependent activity although it loses its glutamine-dependent activity, so that it is applicable for the industrial conversion of 5'-XMP into 5'-GMP. Through scrutiny into the biochemical mechanism of 5'-XMP aminase, the present inventors have developed a glutaminase-suppressed ammonia-specific 5'-XMP aminase and successfully realized its enhanced activity in culture fluid, leading to the present invention.

DISCLOSURE OF THE INVENTION

It is therefore an object of the present invention to provide an ammonia-specific 5'-xanthylic acid (XMP) aminase mutant having enhanced activity, which is prepared by imparting ammonia specificity to a wild-type 5'-XMP aminase or a 5'-XMP aminase mutant having enhanced activity.

It is another object of the present invention to provide a method of preparing an ammonia-specific 5'-XMP aminase mutant having enhanced activity.

It is a further object of the present invention to provide a nucleic acid molecule encoding an ammonia-specific 5'-XMP aminase mutant.

It is a still further object of the present invention to provide an expression vector carrying a nucleic acid molecule encoding an ammonia-specific 5'-XMP aminase mutant.

It is still another object of the present invention to provide a transformant transformed with the above expression vector.

It is yet another object of the present invention to provide a method of converting 5'-XMP to 5'-GMP using an ammonia-specific 5'-XMP aminase mutant.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
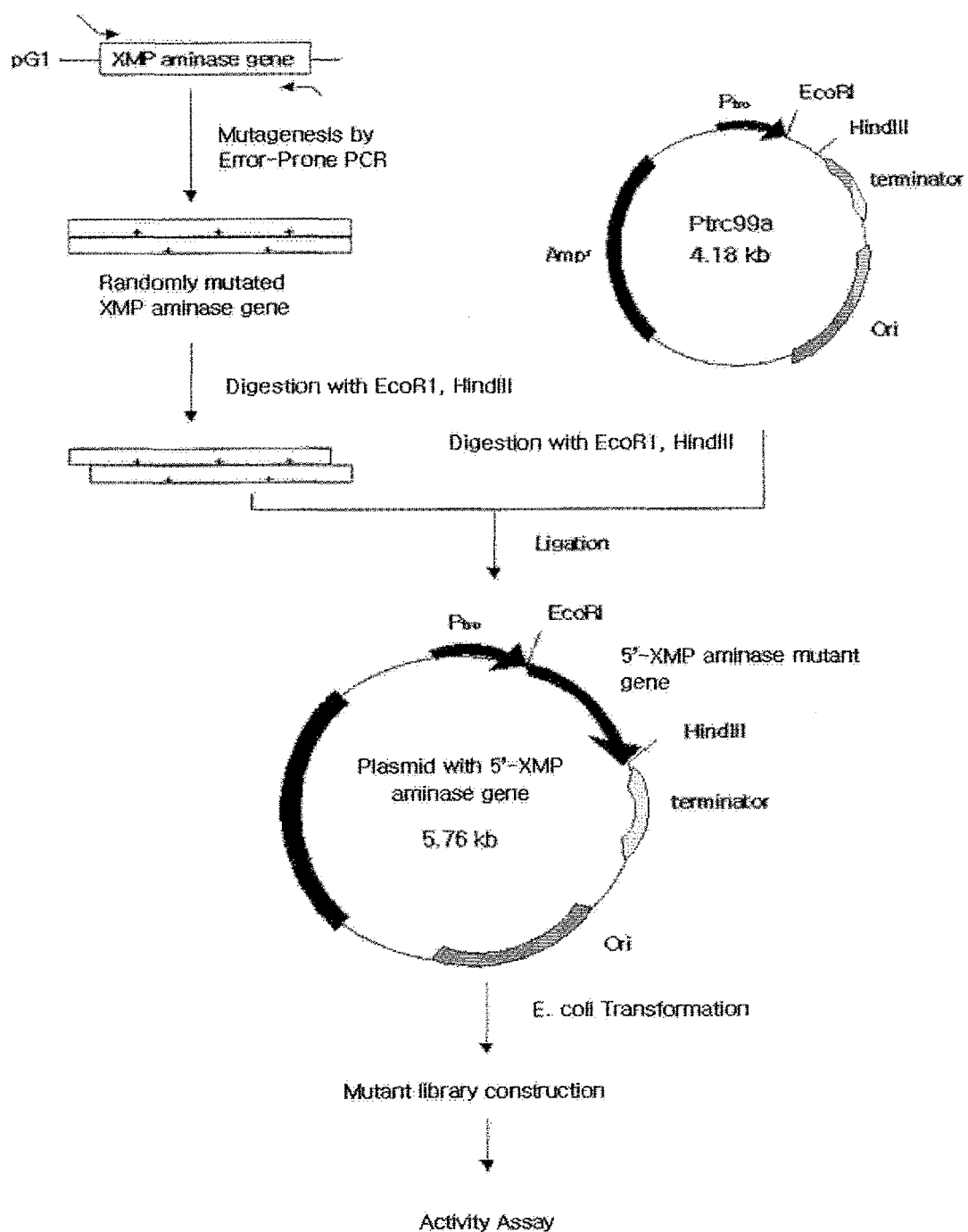
FIG. 1 schematically shows a process for producing a 5'-XMP aminase mutant, comprising constructing a 5'-XMP aminase mutant library by random mutagenesis and screening the mutant library to select for highly active 5'-XMP aminase mutants.

In accordance with one aspect, there is provided an ammonia-specific 5'-xanthylic acid (XMP) aminase mutant which has enhanced activity. The ammonia-specific 5'-XMP aminase mutant may preferably be prepared from *Escherichia coli*-derived wild-type amylase or a mutant thereof having enhanced activity.

In greater detail, site-directed mutagenesis for imparting ammonia specificity is conducted on the wild-type 5'-XMP aminase derived from *Escherichia coli* or on a randomly mutated 5'-XMP aminase derived from an *Escherichia coli* mutant having enhanced-activity to prepare an ammonia-specific 5'-XMP aminase mutant, derived from *Escherichia coli*, which thus has further enhanced activity.

In an embodiment, in order to obtain a vector expressing 5'-XMP aminase, a vector carrying a gene 1,578 bp long (SEQ ID NO.: 1) encoding 5'-XMP aminase derived from *Escherichia coli* K12 was prepared, followed by a mutant inducing polymerization chain reaction (error-prone PCR) with the vector as a template. As a result, 5'-XMP aminase mutant DNA molecules, into which mutations were randomly introduced, were obtained. The mutant DNA molecules were inserted into an expression vector suitable for expressing 5'-XMP aminase mutants. The resulting vectors were transformed into an *E. coli* strain deficient in the 5'-XMP aminase gene to construct a mutant library.

Since the *E. coli* deficient in the 5'-XMP aminase gene is able to grow only when transformed with a vector expressing a mutant having 5'-XMP aminase activity, only active mutants of 5'-XMP aminase were obtained from the mutant library.

To select *E. coli* clones transformed with a vector expressing a highly active mutant form of 5'-XMP aminase from grown *E. coli* colonies, the conversion of 5'-XMP into 5'-GMP was performed on 98-well microplates. After the reaction was terminated, *E. coli* clones producing 5'-XMP aminase having increased activity were selected by comparing absorbance values with a control.

The nucleotide sequences of 5'-XMP aminase mutants having enhanced activity were determined using a known method. Comparison of nucleotide sequences between 5'-XMP aminase mutants and wild-type 5'-XMP aminase disclosed that six selected mutants of 5'-XMP aminase had new amino acid sequences each altered in two, two, four, four, three and six amino acid residues, and were designated "5'-XMP aminase G3", "5'-XMP aminase F12", "5'-XMP aminase F63", "5'-XMP aminase G3-1", "5'-XMP aminase F12-1" and "5'-XMP aminase F63-1", respectively.

Each mutant has an alteration in its amino acid sequence compared to that of a wild-type 5'-XMP aminase, as described in detail in the following. The G3 mutant has an amino acid sequence (SEQ ID NO.: 4) in which amino acid residues at positions 52 and 191 are replaced by cysteine and threonine, respectively. The F12 mutant has an amino acid sequence (SEQ ID NO.: 6) in which amino acid residues at positions 93 and 152 are replaced by valine and proline, respectively. The F63 mutant has a valine residue at position 93, an alanine residue at position 113, a threonine residue at position 191, and a glycine residue at position 467 in the amino acid sequence (SEQ ID NO.: 8). As for the G3-1 mutant, its amino acid sequence (SEQ ID NO.: 10) features a cysteine residue at position 52, a threonine residue at position 191, an arginine reside at position 253, and an isoleucine residue at position 454. The F12-1 mutant has an amino acid sequence (SEQ ID NO.: 12) in which amino acid residues at positions 93, 152 and 454 are replaced by valine, proline and isoleucine, respectively. In the F63-1 mutant (SEQ ID NO.: 14), valine is found at position 93, isoleucine at position 100, alanine at position 113, threonine at position 191, isoleucine at position 454, and glycine at position 467.

Subsequently, in order to prepare ammonia-specific 5'-XMP aminase, the wild-type 5'-XMP aminase derived from *Escherichia coli* and the activity-enhanced mutants G3-1, F12-1 and F63-1 were subjected to site-directed mutagenesis for replacing the cysteine residue at position 86 within the glutaminase active site with alanine. Following the site-directed mutagenesis, the resulting mutants were designated G1C (SEQ ID NO.: 16), G3C (SEQ ID NO.: 18), F12C (SEQ ID NO.: 20), and F63C (SEQ ID NO.: 22), respectively. The nucleotide sequences of these 5'-XMP aminase mutants were determined using a known base sequencing method. The resulting mutants were found to utilize, as an amine donor, glutamine at very low efficiency, but external ammonia at great efficiency.

In accordance with a preferable embodiment of this aspect of the present invention, thus, there is provided an ammonia-specific 5'-XMP aminase mutant having the amino acid sequence of SEQ ID NO.: 16, 18, 20 or 22.

In the following Example section, only methods of preparing the ammonia-specific 5'-XMP aminase mutants having SEQ ID NOS.: 16, 18, 20 and 22 are described, along with their activities, but it will be fully understood by those skilled in the art that ammonia-specific 5'-XMP aminase mutants having enhanced activity can be readily prepared by imparting ammonia specificity to the activity-enhanced 5'-XMP aminase mutants of SEQ ID NOS.: 4, 6 and 8.

Also, only 5'-XMP mutants having amino acid sequences in which the cysteine residue at position 86 is replaced by alanine are described in the following Example section, but those skilled in the art will fully understand that ammonia-specific 5'-XMP aminase mutants can be readily obtained when an amino acid residue, such as serine or glycine, rather than alanine, is introduced using a site-directed mutagenesis technique.

Further, the ammonia-specific 5'-XMP aminase mutant of the present invention not only means proteins each having the amino acid sequence of SEQ ID No. 16, 18, 20 or 22, but also includes a functional equivalent exerting the activity identical to these mutant proteins. The term "functional equivalent", as used herein, refers to a protein that has a sequence different from an amino acid sequence of the ammonia-specific 5'-XMP aminase mutant of the present invention, by a deletion, an insertion, a non-conservative or conservative substitution or combinations thereof in one more amino acid residues, and that exerts the ammonia-specific 5'-XMP aminase activity almost exactly as high as that of the ammonia-specific 5'-XMP aminase mutant of the present invention. Amino acid exchanges in proteins and peptides which do not generally alter the activity of the proteins or peptides are known in the art (H. Neurath, R. L. Hill, The Proteins, Academic Press, New York, 1979).

When the ammonia-specific 5'-XMP aminase mutants of the present invention are expressed using a constitutive expression system, as will be described later, they are found to have higher activity per reaction solution than the native form. In detail, the increased activity is measured to amount to 1.6 times for the G1C 5'-XMP aminase mutant, 1.4 times for the G3C 5'-XMP aminase mutant, 1.4 times for the F12C 5'-XMP aminase mutant, and 1.45 times for the F63C 5'-XMP aminase mutant, compared with the native form. Thus, the ammonia-specific 5'-XMP aminase mutants may be highly useful in the production of 5'-GMP.

The ammonia-specific 5'-XMP aminase mutants according to the present invention may be prepared by a chemical synthesis method (Merrifield, J. Amer. Chem. Soc. 85:2149-2156, 1963), or by a DNA recombinant method (Sambrook et al., Molecular Cloning, Cold Spring Harbor Laboratory Press, New York, USA, 2$^{nd}$ Ed., 1989). When a genetic recombination technique is used, an ammonia-specific 5'-XMP aminase mutant may be obtained by inserting a nucleic acid sequence encoding the ammonia-specific 5'-XMP aminase mutant into a suitable expression vector, transforming the recombinant expression vector into a host cell, culturing the host cell to express the ammonia-specific 5'-XMP aminase mutant, and recovering the ammonia-specific 5'-XMP aminase mutant from the host cell.

In accordance with another aspect of the present invention, therefore, there is provided a method for preparing an ammonia-specific 5'-XMP mutant having enhanced activity. In greater detail, the present invention provides a method for preparing an ammonia-specific 5'-XMP aminase mutant devoid of glutaminase activity, which exhibits minimal in vivo activity and thus is greatly reduced in cytotoxicity, but with ammonia-dependent activity remaining unchanged, thereby being able to effectively convert 5'-XMP to 5'-GMP.

In a preferred embodiment of this aspect of the present invention, the cysteine residue at position 86 within the glutaminase active site of E. coli-derived 5'-XMP aminase is replaced with a different amino acid through site-directed mutagenesis, so that the new amino acid at position 86 cannot form a γ-glutamyl thioester bond with the glutamic acid at 183, thereby suppressing the glutamine-dependent activity but conserving the ammonia-dependent activity. In a more preferred embodiment, the method for preparing an ammonia-specific 5'-XMP aminase mutant is effected by replacing the cysteine residue at position 86 of Escherichia coli-derived 5'-XMP aminase with alanine.

In a particularly preferred embodiment of this aspect, the ammonia-specific 5'-XMP aminase mutant is prepared from the wild-type 5'-XMP aminase of Escherichia coli or from mutants thereof having enhanced activity.

In a further particularly preferred embodiment of this aspect of the present invention, the ammonia-specific 5'-XMP mutant is prepared by replacing alanine for the cysteine residue at position 86 of the wild-type 5'-XMP aminase derived from Escherichia coli or of the 5'-XMP aminase mutant having the amino acid sequence of SEQ ID NO.: 4, 6, 8, 10, 12 or 14, provided according to embodiments of the present invention, having enhanced activity.

In a further aspect, the present invention pertains to a nucleic acid molecule encoding an ammonia-specific 5'-XMP aminase mutant.

In a preferred embodiment of this aspect of the present invention, the ammonia-specific 5'-XMP aminase mutant G1C of SEQ ID NO.: 16 is encoded by the nucleic acid molecule of SEQ ID NO.: 15, the ammonia-specific 5'-XMP aminase mutant G3C of SEQ ID NO.: 18 by the nucleic acid molecule of SEQ ID NO.: 17, the ammonia-specific 5'-XMP aminase mutant F12C of SEQ ID NO.: 20 by the nucleic acid molecule of SEQ ID NO.: 19, and the ammonia-specific 5'-XMP aminase mutant F63C of SEQ ID NO.: 22 by the nucleic acid molecule of SEQ ID NO.: 21. The sequences of the nucleic acid molecules may be single-stranded or double-stranded, and may be RNA (mRNA) formed by a substitution of uracil (U) for thymine (T) in a DNA molecule or sequence.

The nucleic acid sequence encoding the ammonia-specific 5'-XMP aminase mutant of the present invention may be introduced into a vector for expressing the mutant so as to be expressed as a protein.

In a still further aspect, the present invention provides an expression vector carrying the nucleic acid molecule encoding the ammonia-specific 5'-XMP aminase mutant.

As used herein, the term "expression vector", which describes a vector capable of expressing a protein of interest in a suitable host cell, refers to a genetic construct that comprises essential regulatory elements to which a gene insert is operably linked in such a manner as to be expressed in a host cell.

By the term "operably linked", as used herein, it is meant that there is a functional linkage between a nucleic acid expression control sequence and a nucleic acid sequence coding for a target protein in such a manner as to perform general functions. For example, a promoter may be operably linked to a nucleic acid coding for a protein, and may affect the expression of the coding nucleic acid sequence. The operable linkage to a recombinant vector may be prepared using a genetic recombination technique that is well known in the art, and site-specific DNA cleavage and ligation may be easily achieved using enzymes generally known in the art. Promoters useful in an expression vector may be those available from the host cells Escherichia spp. or Bacillus spp. Examples of promoters useful in Escherichia spp. include trc promoter, trp promoter, lac promoter, recA promoter, λPL promoter, lpp promoter and T7 promoter. As for Bacillus species as host cells, useful promoters obtained therefrom may be exemplified by SPOL promoter, SPO2 promoter and penP promoter. The initiation and stop codons are necessary in order to be functional in an individual to whom a genetic construct has been administered, and must be in frame with the coding sequence. An expression vector may also include a selectable marker that allows the selection of host cells containing the vector. A replicable expression vector may include a replication origin.

In one practice of the present invention, expression vectors, pCJ1-G1C, pCJ1-G3C, pCJ1-F12C and pCJ1-F63C, each carrying a gene encoding an ammonia-specific 5'-XMP aminase mutant, were constructed, the structures of which are shown in schematic diagrams of FIGS. 13, 14, 15 and 16, respectively. These expression vectors were individually introduced into *Escherichia coli* DH5α to obtain transformed *Escherichia coli*. The transformants thus produced were designated "*Escherichia coli* DH5α/pCJ1-G1C", "*Escherichia coli* DH5α/pCJ1-G3C", "*Escherichia coli* DH5α/pCJ1-F12C" and "*Escherichia coli* DH5 α/pCJ1-F63C", respectively, and were deposited at the Korean Culture Center of Microorganisms (KCCM) on Dec. 2, 2005, with accession numbers KCCM-10715P, KCCM-10717P, KCCM-10721P and KCCM-10720, respectively.

Therefore, in still another aspect, the present invention provides a transformant transformed with one of the expression vectors.

Transformation includes any method by which nucleic acids can be introduced into organisms, cells, tissues or organs, and, as known in the art, may be performed using at least one suitably selected from standard techniques that depend on host cells. These methods include, but are not limited to, electroporation, protoplast fusion, calcium phosphate ($CaPO_4$) precipitation, calcium chloride ($CaCl_2$) precipitation, agitation with silicon carbide fiber, *agrobacterium*-mediated transformation, and PEG-, dextran sulfate-mediated transformation, and lipofectamine-mediated transformation.

Host cells most suitable for objects may be selected and used because expression levels, modification, or the like of proteins vary depending on host cells into which an expression vector expressing the 5'-XMP aminase mutant of the present invention is transformed. Host cells include, but are not limited to, prokaryotic cells such as *Escherichia coli*, *Bacillus subtilis*, *Streptomyces*, *Pseudomonas*, *Proteus mirabilis* or *Staphylococcus*.

Also, lower eukaryotic cells, such as fungi (e.g., *Aspergillus* species) and yeasts (e.g., *Pichia pastoris*, *Saccharomyces cerevisiae*, *Schizosaccharomyces*, *Neurospora crassa*) may be utilized as host cells.

In still another aspect, the present invention provides a method for preparing a 5'-XMP aminase mutant, comprising culturing the transformant and isolating a mutant protein of 5'-XMP aminase from the culture fluid.

The cultivation of host cells (transformants) transformed with an expression vector expressing the ammonia-specific 5'-XMP aminase mutant of the present invention may be performed under culture conditions suitable for expressing the target protein, ammonia-specific 5'-XMP aminase mutant, using a method generally known to those skilled in the art.

The proteins of the present invention, expressed in host cells, may be purified by conventional methods. For example, salting out (e.g., ammonium sulfate precipitation, sodium phosphate precipitation, etc.), solvent precipitation (e.g., protein fraction precipitation using acetone, ethanol, etc.), dialysis, gel filtration, chromatographic methods such as ion exchange chromatography and reverse phase chromatography, and ultrafiltration may be used, separately or in combination, for purifying the ammonia-specific 5'-XMPaminiase mutant proteins of the present invention.

A better understanding of the present invention may be obtained through the following examples which are set forth to illustrate, but are not to be construed as the limit of the present invention.

EXAMPLE 1

Construction of 5'-XMP Aminase Mutant Library

Random mutations were introduced into a 5'-XMP aminase gene by a mutant inducing polymerization chain reaction (error-prone PCR), so as to prepare various 5'-XMP aminase mutants as follows.

First, a 5'-XMP aminase gene (SEQ ID NO.: 1) of 1,578 bp derived from *Escherichia coli* was operably linked to an expression vector, pTrc99a, which includes a trc promoter and a replication origin functional in *Escherichia coli*, thus yielding a recombinant plasmid, pGl, as a template for error-prone PCR. This PCR was performed with a pair of an N-terminal primer, represented by SEQ ID NO.: 23, and a C-terminal primer, represented by SEQ ID NO.: 24. The primers were synthesized based on the nucleotide sequence of the 5'-XMP aminase gene derived from *E. coli*.

SEQ ID NO.: 23: 5'CGCGAATTCATGACGGAAAACATTCATAA 3'

SEQ ID NO.: 24: 5'CTAGTCTAGATCATTCCCACTCAATGGT 3'

A PCR mixture was made to contain of 0.4 mM of the N-primer and the C-primer each, 5 ng of the recombinant plasmid pGl, 10 mM Tris-HCl (pH 8.3), 50 mM KCl, 7 mM $MgCl_2$, 0.1 mM $MnCl_2$, 0.2 mM DATP, 0.2 mM dGTP, 1 mM dCTP, 1 mM dTTP and 5 units of Taq polymerase, in a final volume of 50 mL. Error-prone PCR was carried out with 25 cycles of denaturation at 94° C. for 1 min, annealing at 50° C. for 1 min, and elongation at 72° C. for 1 min, followed by final elongation at 72° C. for 7 min, to produce mutant genes.

PCR products thus produced were separated by electrophoresis on agarose gel. The gel-purified DNA fragments were digested with EcoRI and HindIII and inserted into an expression vector, pTrc99a, useful for expressing 5'-XMP aminase, thus constructing recombinant plasmids. The recombinant vectors carrying the 5'-XMP aminase gene mutants were introduced into *Escherichia coli* BW (guaa gene-knockout strain) to construct a mutant library of 5'-XMP aminase. A guaA gene-deleted *Escherichia coli* BW strain was prepared using an ordinary molecular biological method (Datsenko K A, 2000, Proc. Natl. Acad. Sci., 97(12), 6640-6645).

EXAMPLE 2

Screening for 5'-XMP Aminase Mutants

A broth of the 5'-XMP aminase mutant library prepared in Example 1 was smeared onto LB plates containing 0.5% bactotryptone, 1% yeast extract, 1% NaCl, 1.5% agar and 0.2 mM IPTG. The grown *Escherichia coli* colonies were cultured in LB medium in deep-well microplates. The culture was then diluted in accordance with the growth degree to give a final volume of 100 mL. 5 ml of xylene was added to each well of the plates, and the plates were incubated at 37° C. for 30 min. 100 ml of a substrate solution preheated to 42° C. was added to each well prior to the incubation of the plates at 42° C. for 20 min. The substrate solution was composed of 30 mM XMP, 13 mM ATP, 16 mM $MgSO_4.7H_2O$ and 40 mM $(NH_4)_2SO_4$ in 16 mM Trizma HCl buffer (pH 8.6). Following the addition of 800 ml of 3.5% perchloric acid to each well to terminate the reaction, 200 mL of the reaction mixture was transferred into a 96-well UV-transparent microplate to measure absorbance at 290 nm. The yield of 5'-GMP was measured and enzyme activities were compared so as to select an *Escherichia coli* JM105 transformant which expressed a 5'-XMP aminase mutant having enhanced activity.

The pG3 plasmid thus obtained, carrying a 5'-XMP aminase mutant gene, and the pGl plasmid carrying a native 5'-XMP aminase gene were digested with proper restriction enzymes, ligated, and subjected to error-prone PCR under the same conditions as in Example 1. The screening for enzyme activity and activity comparison resulted in the obtainment of plasmids pF12, pF63, pCJ-G3-1, pCJ-F12-1 and pCJ-F63-1, which expressed 5'-XMP aminase having enhanced activity relative to the parent enzyme.

FIG. 1 schematically illustrates a process for producing a 5'-XMP aminase mutant having enhanced activity, described in Examples 1 and 2.

The scale of the 5'-XMP aminase mutant library and descriptions of mutants prepared in Example 2 are summarized in Table 1, below.

TABLE 1

Molecular evolution of 5'-XMP aminase and selected mutants

| Parent Gene | 1R<br>Native guaA<br>gene | 2R<br>Native gene and G3 mutant<br>gene |
|---|---|---|
| Library Construction method | Error-prone PCR | Restriction enzyme digestion and Error-prone PCR |
| Library scale | >~10$^5$ | >~1,500 |
| 1$^{st}$ Screening | ~2 × 10$^3$ | ~1,500 |
| 2$^{nd}$ Screening | 73 colonies | 66 colonies |
| Obtained mutants | G3 | F12, F63, G3-1, F12-1, F63-1 |

EXAMPLE 3

Base Sequencing of Genes Encoding 5'-XMP Aminase Mutants

Nucleotide sequences of 5'-XMP aminase mutants, prepared in Examples 1 and 2, were analyzed using an automatic sequencer model ABI3730x1 (Applied Biosystems). The nucleotide sequences were identified as SEQ ID NO.: 3 for the G3 mutant, SEQ ID NO.: 5 for the F12 mutant, SEQ ID NO.: 7 for the F63 mutant, SEQ ID NO.: 9 for the G3-1 mutant, SEQ ID NO.: 11 for the F12-1 mutant, and SEQ ID NO.: 13 for the F63-1 mutant. Also, the amino acid sequences deduced from the nucleotide sequences are represented, respectively, by SEQ ID NO.: 4 (G3), SEQ ID NO.: 6 (F12), SEQ ID NO.: 8 (F63), SEQ ID NO.: 10 (G3-1), SEQ ID NO.: 12 (F12-1), and SEQ ID NO.: 14 (F63-1). Schematic maps of plasmids carrying genes encoding the mutants G3, F12, F63, G3-1, F12-1 and F63-1 are given in FIGS. 3, 4, 5, 6, 7 and 8, respectively.

In greater detail, the amino acid sequence of the G3 mutant was deduced from the nucleotide sequence of the highly active G3 5'-XMP aminase mutant gene contained in the pG3 plasmid, and is represented by SEQ ID NO.: 4. The amino acid sequence of the F12 mutant was deduced from the nucleotide sequence of the highly active F12 5'-XMP aminase mutant gene contained in the pF12 plasmid, and is represented by SEQ ID NO.: 6. Likewise, the amino acid sequence of the F63 mutant was deduced from the nucleotide sequence of the highly active F63 5'-XMP aminase mutant gene contained in the pF63 plasmid, and is represented by SEQ ID NO.: 8. The amino acid sequence of the G3-1 mutant was deduced from the nucleotide sequence of the highly active G3-1 5'-XMP aminase mutant gene contained in the Pg3-1 plasmid, and is represented by SEQ ID NO.: 10. The amino acid sequence of the F12-1 mutant was deduced from the nucleotide sequence of the highly active F12-1 5'-XMP aminase mutant gene contained in the pCJ-F12-1 plasmid, and is represented by SEQ ID NO.: 12. The amino acid sequence of the F63-1 mutant was deduced from the nucleotide sequence of the highly active F63-1 5'-XMP aminase mutant gene contained in the pCJ-F63-1 plasmid, and is represented by SEQ ID NO.: 14.

When the amino acid sequences of the highly active 5'-XMP aminase mutants G3, F12, F63, G3-1, F12-1 and F63-1 were compared with the amino acid sequence of native 5'-XMP aminase, represented by SEQ ID NO.: 2, they were found to have amino acid substitutions for two, two, four, four, three and six amino acid residues, respectively.

In detail, the G3 mutant has an amino acid sequence in which amino acid residues at positions 52 and 191 are replaced by cysteine and threonine, respectively. The F12 mutant has an amino acid sequence in which amino acid residues at positions 93 and 152 are replaced by valine and proline, respectively. The F63 mutant has an amino acid sequence featuring a valine residue at position 93, an alanine residue at position 113, a threonine residue at position 191 and a glycine residue at position 467. The G3-1 mutant has an amino acid sequence in which amino acid residues at positions 52, 191, 253 and 454 are replaced by cysteine, threonine, arginine and isoleucine, respectively. The F12-1 mutant has an amino acid sequence in which amino acid residues at positions 93, 152 and 454 are replaced by valine, proline and isoleucine, respectively. The F63-1 mutant has an amino acid sequence in which amino acid residue substitutions exist at position 93 for valine, position 100 for isoleucine, position 113 for alanine, position 191 for threonine, position 454 for isoleucine and position 467 for glycine. The results of amino acid sequence analysis and enzyme activity assay indicate that the G3, F12, F63, G3-1, F12-1 and F63-1 mutants are novel 5'-XMP aminase mutant forms, each of which has an amino acid sequence that differs from that of native *E. coli* 5'-XMP aminase and is highly active.

EXAMPLE 4

Construction of Constitutive Expression Vector of 5'-XMP Mutant

The highly active 5'-XMP aminase mutants prepared above were expressed using a constitutive expression vector as follows.

5'-XMP aminase wild-type and mutant genes were operably linked to the constitutive expression vector pECG117-CJ1, which includes a CJ1 promoter and a replication origin functional in *Escherichia coli* and *Corynebacterium ammoniagenes*, so as to produce recombinant plasmids. Error-prone PCR was performed with a set of the N-terminal primer (guaA-f) of SEQ ID NO.: 25 and the C-terminal primer (guaA-r) of SEQ ID NO.: 26. These primers were synthesized on the basis of the nucleotide sequence of the 5'-XMP aminase gene derived from *Escherichia coli*.

```
SEQ ID NO.: 25:
5' ACGTGCCGGCATGACGGAAAACATTCATAAGC 3'

SEQ ID NO.: 26:
5' ACGTGGATCCTCATTCCCACTCAATGGTAGC 3'
```

A PCR mixture was composed of 0.4 mM of the N-primer and the C-primer each, 5 ng of the recombinant plasmid pGl, pCJ-G3-1, pCJ-F12-1 or pCJ-F63-1, 10 mM Tris-HCl (pH 8.3), 50 mM KCl, 7 mM MgCl$_2$, 0.2 mM DATP, 0.2 mM dGTP, 0.2 mM dCTP, 0.2 mM dTTP and 5 units of Pfu polymerase, in a final volume of 50 mL. Error-prone PCR was carried out with 25 cycles of denaturation at 94° C. for 1 min, annealing at 50° C. for 1 min and elongation at 72° C. for 1 min, followed by final elongation at 72° C. for 5 min.

Figure 2:
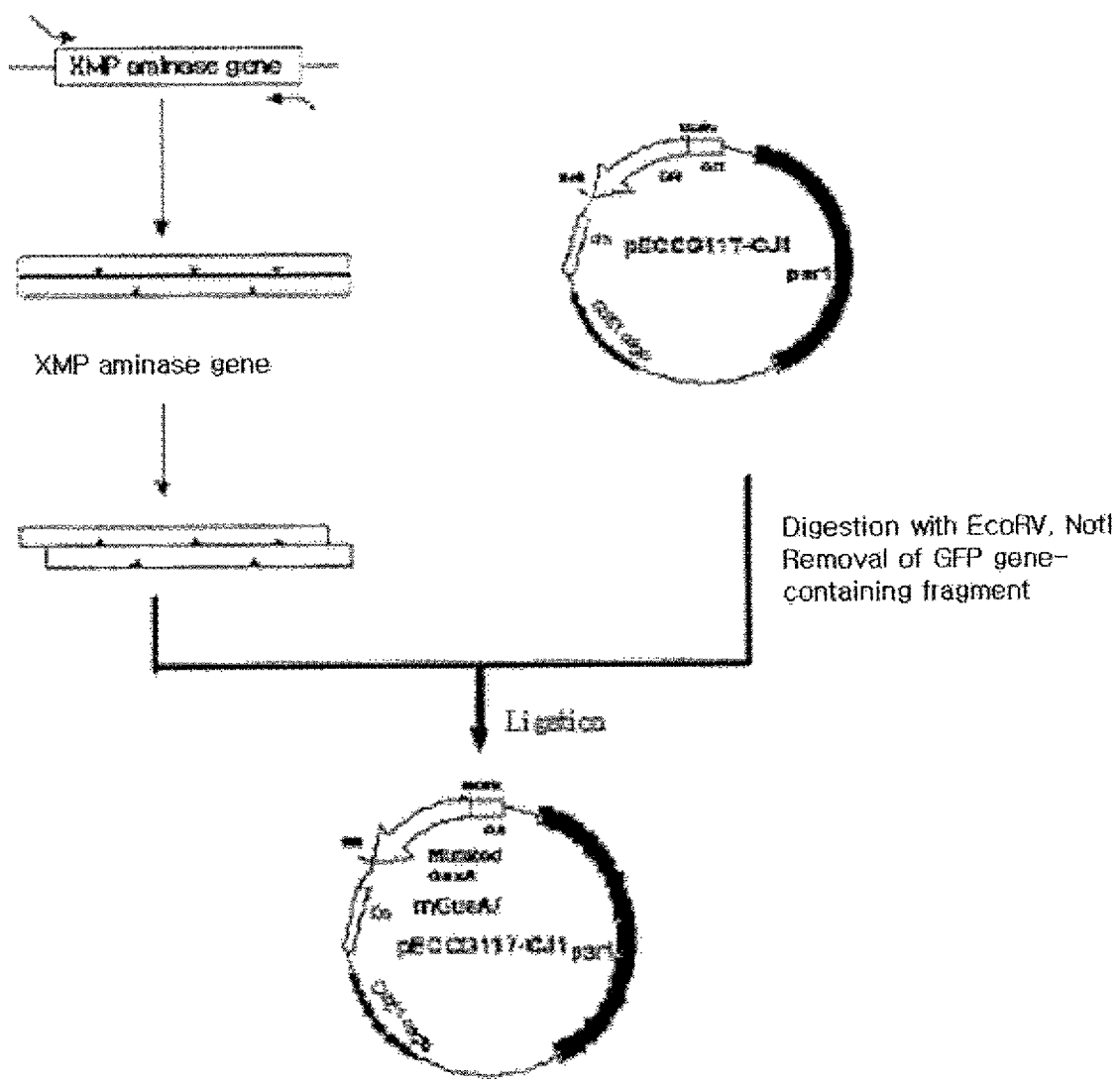
FIG. 2 schematically shows a process for introducing a randomly mutated gene encoding the highly active 5'-XMP aminase mutant into a constitutive expression vector.
Figure 3:
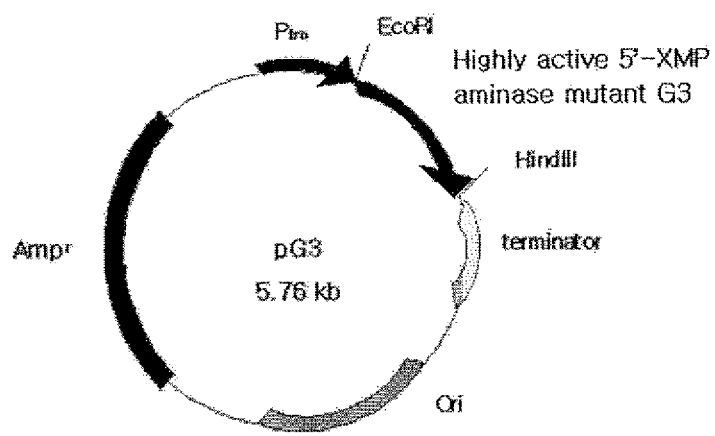
FIG. 3 is a schematic view showing an expression vector pG3 carrying a gene encoding a highly active 5'-XMP aminase mutant, G3.
Figure 4:
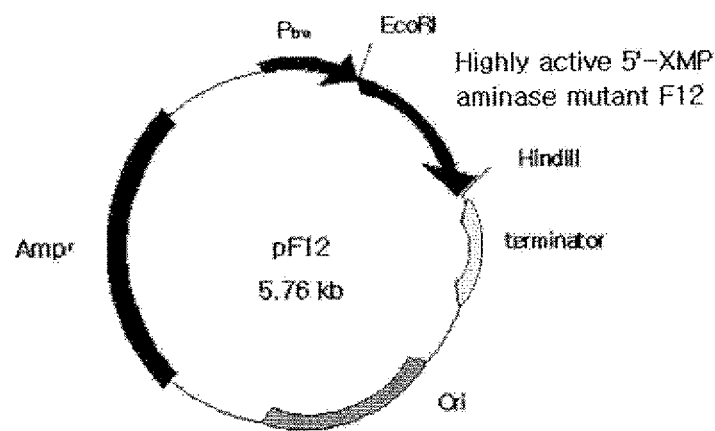
FIG. 4 is a schematic view showing an expression vector pF12 carrying a gene encoding a highly active 5'-XMP aminase mutant, F12.
Figure 5:
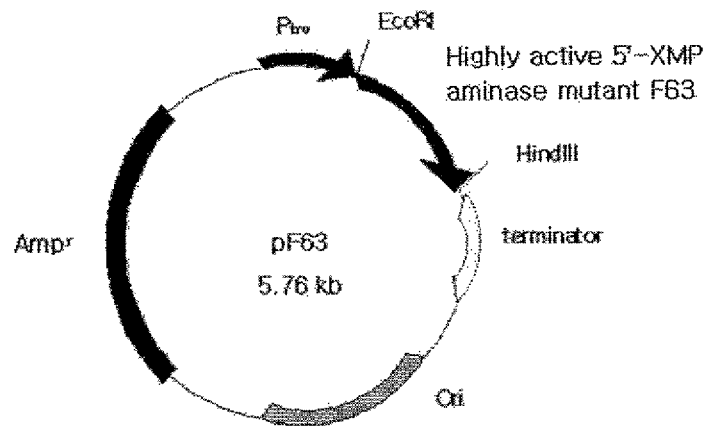
FIG. 5 is a schematic view showing an expression vector pF63 carrying a gene encoding a highly active 5'-XMP aminase mutant, F63.
Figure 6:
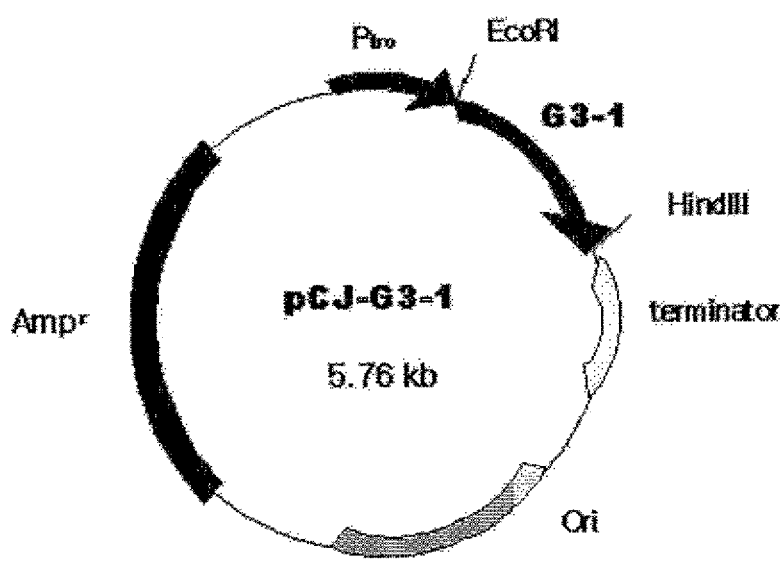
FIG. 6 is a schematic view showing an expression vector pCJ-G3-1 carrying a gene encoding a highly active 5'-XMP aminase mutant, G3-1.
Figure 7:
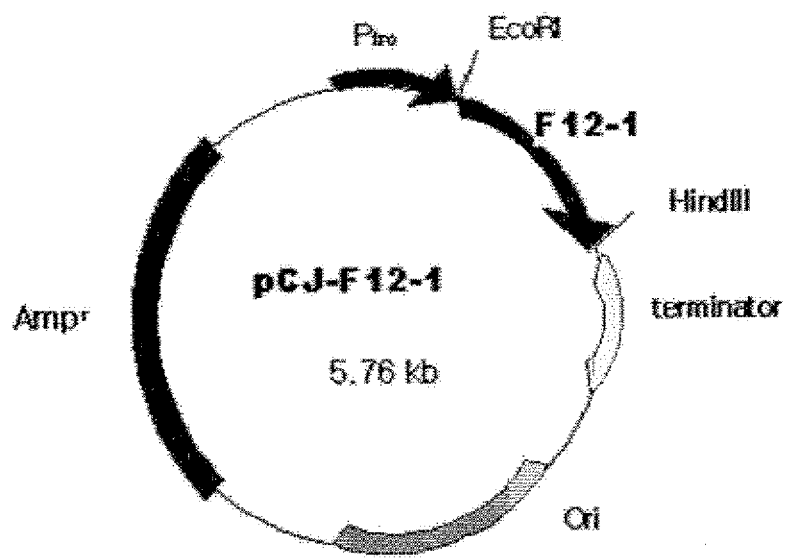
FIG. 7 is a schematic view showing an expression vector pCJ-F12-1 carrying a gene encoding a highly active 5'-XMP aminase mutant, F12-1.
Figure 8:
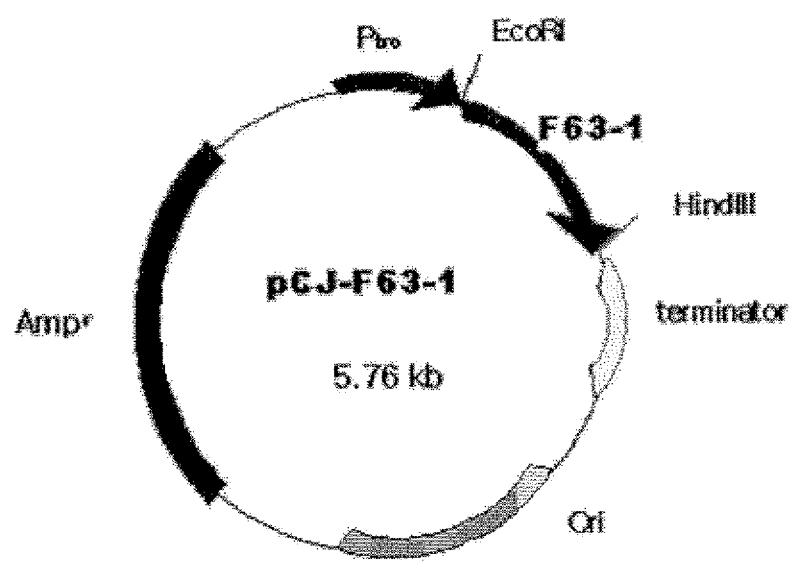
FIG. 8 is a schematic view showing an expression vector pCJ-F63-1 carrying a gene encoding a highly active 5'-XMP aminase mutant, F63-1.
Figure 9:
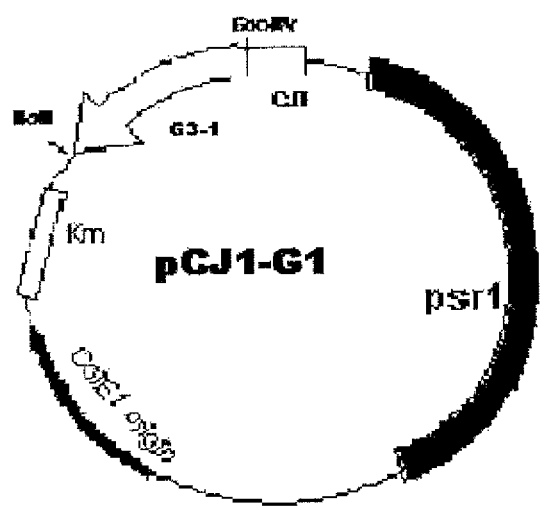
FIG. 9 is a schematic view showing an expression vector pCJ1-G1 carrying a gene encoding a wild-type 5'-XMP aminase, G1.
Figure 10:
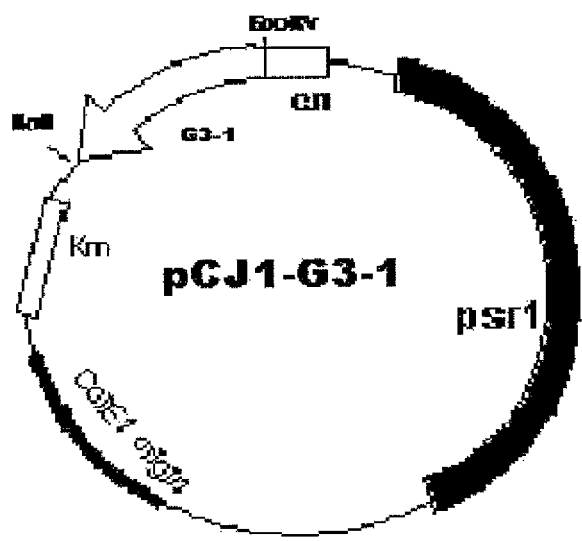
FIG. 10 is a schematic view showing an expression vector pCJ1-G3-1 carrying a gene encoding a highly active 5'-XMP aminase mutant, G3-1.
Figure 11:
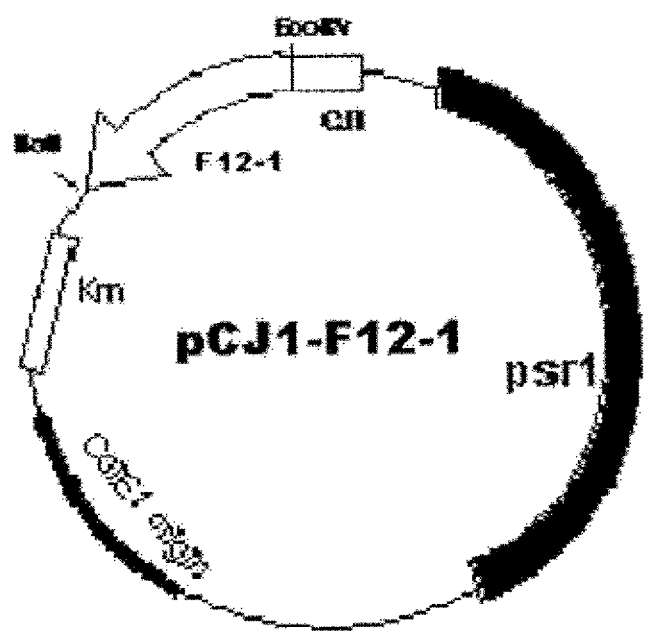
FIG. 11 is a schematic view showing an expression vector pCJ1-F12-1 carrying a gene encoding a highly active 5'-XMP aminase mutant, F12-1.
Figure 12:
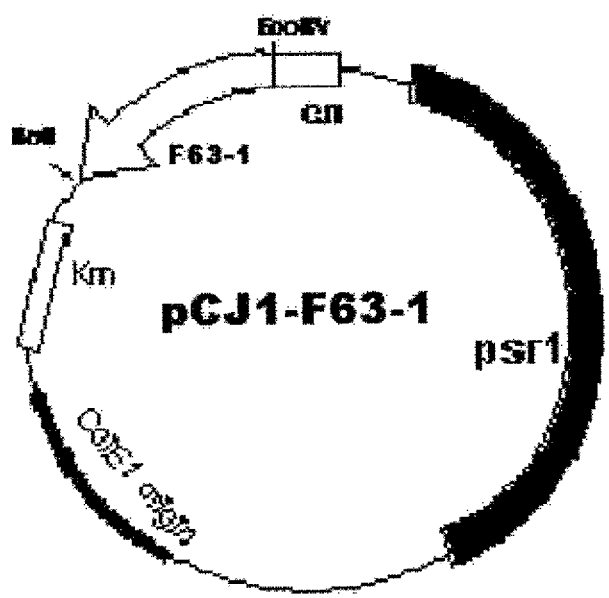
FIG. 12 is a schematic view showing an expression vector pCJ1-F63-1 carrying a gene encoding a highly active 5'-XMP aminase mutant, F63-1.
Figure 13:
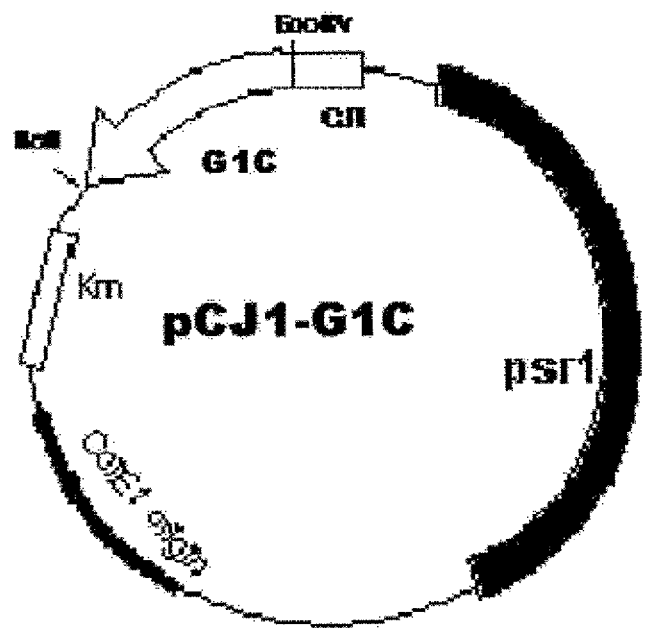
FIG. 13 is a schematic view showing an expression vector pCJ1-G1C carrying a gene encoding an ammonia-specific 5'-XMP aminase mutant, G1C.
Figure 14:
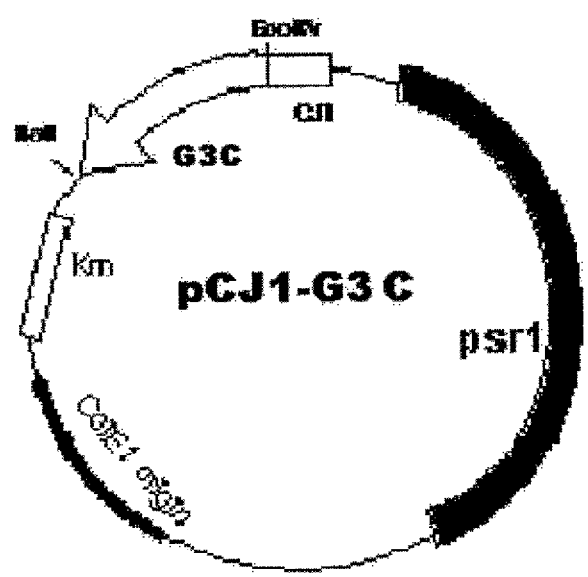
FIG. 14 is a schematic view showing an expression vector pCJ1-G3C carrying a gene encoding an ammonia-specific 5'-XMP aminase mutant, G3C.
Figure 15:
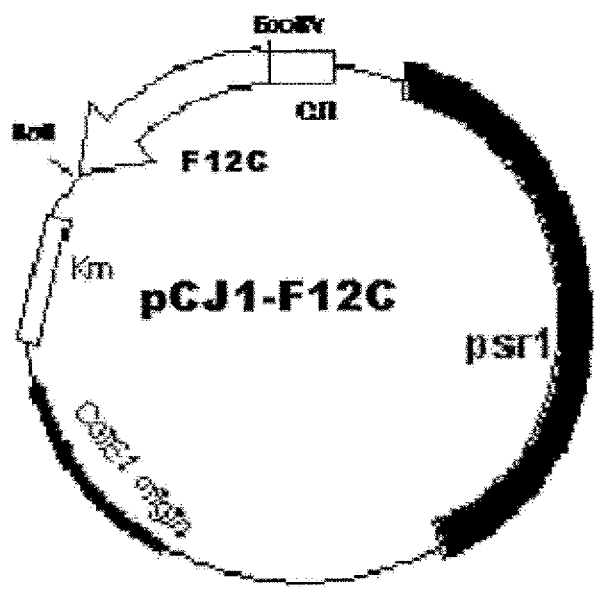
FIG. 15 is a schematic view showing an expression vector pCJ1-F12C carrying a gene encoding an ammonia-specific 5'-XMP aminase mutant, F12C.
Figure 16:
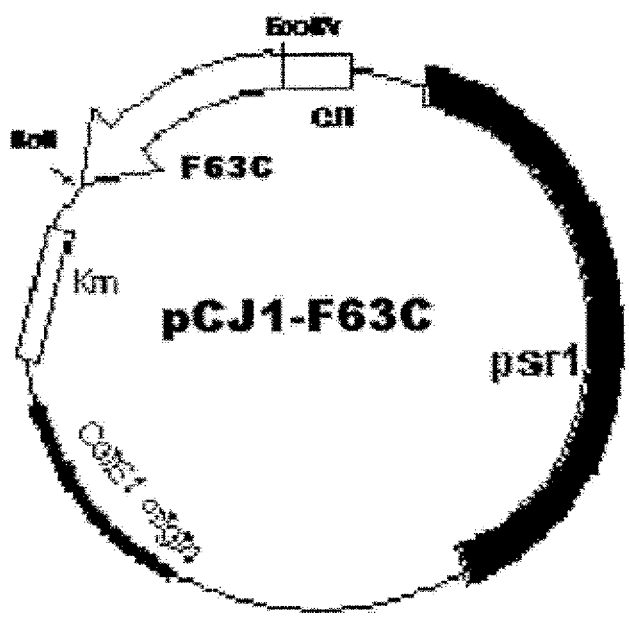
FIG. 16 is a schematic view showing an expression vector pCJ1-F63C carrying a gene encoding an ammonia-specific 5'-XMP aminase mutant, F63C.

PCR products thus produced were separated by electrophoresis on agarose gel. The gel-purified DNA fragments were digested with NaeI and BamHI and inserted into an expression vector, pECG117-CJ1, useful for expressing 5'-XMP aminase, to construct recombinant plasmids (FIG. 2). The recombinant vectors carrying the 5'-XMP aminase wild-type and mutant genes were designated pCJ1-G1 (wild-type), pCJ1-G3-1, pCJ1-F12-1 and pCJ1-F63-1, respectively, the structures of which are shown in schematic diagrams of FIGS. 9, 10, 11 and 12, respectively.

EXAMPLE 5

Production of Ammonia-Specific 5'-XMP Aminase

Ammonia-specific 5'-XMP aminase was produced by taking advantage of wild-type 5'-XMP aminase and the mutants of the highly active 5'-XMP aminase prepared in the above examples. In this regard, a pair of primers was designed to introduce a mutation from a cysteine residue at position 86 to alanine, and was represented by SEQ ID NOS.: 27 and 28.

```
SEQ ID NO.: 27:
5'CCGGTATTCGGCGTTGCATATGGCATGCAGACCATG 3'

SEQ ID NO.: 28:
5'CATGGTCTGCATGCCATATGCAACGCCGAATACCGG 3'
```

In the presence of these primers, site-directed mutagenesis was performed using a QuickChange II XL Site-Directed Mutagenesis kit, commercially available from Stratagene, according to the protocol provided by the manufacturer. Plasmids were isolated from the colonies formed and used to determine the nucleotide sequences of the genes thus obtained. As a result, novel 5'-XMP mutants, in which, on the basis of the wild type 5'-XMP aminase or the mutants thereof, an alanine residue was substituted for cysteine at position 86, were obtained and designated G1C, G3C, F12C and F63C, respectively.

In order to examine whether the correct mutation was introduced at the desired position, nucleotide sequences of 5'-XMP aminase mutants were analyzed using an automatic sequencer ABI3730x1, manufactured by Applied Biosystems. The nucleotide sequences were identified as SEQ ID NO.: 15 (G1C), SEQ ID NO.: 17 (G3C), SEQ ID NO.: 19 (F12C), AND SEQ ID NO.: 21 (F63C). Plasmids carrying genes encoding the 5'-XMP aminase mutants were constructed and designated pCJ1-G1C, pCJ1-G3C, pCJ1-F12C and pCJ1-F63C, respectively, the schematic maps of which are given in FIGS. 13, 14, 15, and 16, respectively.

EXAMPLE 6

Evaluation of Activity of the 5'-XMP Aminase Mutants

The specific activity of 5'-XMP aminase was assessed as follows. First, protein expression levels were measured on an SDS-PAGE gel using an analyzer for protein concentration. As a result, the 5'-XMP aminase mutants exhibited similar expression levels to each other, indicating that the enhanced activity of the 5'-XMP aminase mutants resulted from the increased specific activity.

The activity of the 5'-XMP aminase mutants was compared with that of the native form, as follows. First, transformants expressing mutants were individually inoculated in 25 ml of a culture medium containing 16 g/L of bactotryptone, 10 g/L of yeast extract, 5 g/L of NaCl and 50 mg/L of kanamycin, and cultured at 37° C. for 12 hrs. After the cultured cells were recovered, 1 mL of each culture fluid was mixed with 20 mL of xylene and incubated at 37° C. for 20 min with agitation at 250 rpm. Then, the reaction mixture was diluted 10-fold before assays for determining reactivity with ammonia were conducted. In this regard, 200 mL of the diluted enzyme solution was mixed with 800 mL of a substrate solution which was composed of 30 mM XMP, 13 mM ATP, 16 mM MgSO$_4$.7H$_2$O and 10 mM (NH$_4$)$_2$SO$_4$ in 200 mM Trizma HCl buffer (pH 8.6), and was incubated at 42° C. for 15 min. 200 mL of the resulting reaction mixture was mixed with 3.8 ml of 0.175% TQA to terminate the reaction, and was subjected to HPLC to determine the amount of produced 5'-GMP. Separately, to measure the catalytic activity of the 5'-XMP aminase mutants with glutamine as a substrate, 200 mL of the 10-fold diluted enzyme solution was mixed with 800 mL of a substrate solution which was composed of 30 mM XMP, 13 mM ATP, 16 mM MgSO$_4$.7H$_2$O and 5 mM L-glutamine in 200 mM Trizma HCl buffer (pH 8.6), followed by incubation at 42° C. for 15 min. The product 5'-GMP was quantitatively analyzed using HPLC. One unit of activity of 5'-XMP aminase was defined as the enzyme amount that forms one micromole of 5'-GMP per minute. HPLC was performed under the following conditions.

Eluent A:

0.02% tetrabutylammonium dihydrogen phosphate 0.2% ammonium dihydrogen phosphate, pH 2.4

Eluent B: acetonitrile

A:B=97:3

Measurement wavelength: 254 nm

Flow rate: 1.0 ml/min

When using ammonia as a substrate, the enzyme activity was measured as follows. 13.61 U/ml was measured in the wild-type 5'-XMP aminase, 17.62 U/ml in the G3-1 mutant aminase, 20.82 U/ml in the F12-1 mutant, and 16.47 U/ml in the F63-1 mutant. As for the ammonia-specific 5'-XMP aminase mutants, 22.64 U/mL was measured in the G1C mutant, 19.30 U/mL in the G3C mutant, F12C ≒ 22.76 U/mL in the F12C mutant, and 19.62 U/mL in the F63C mutant.

On the other hand, when using L-glutamine as a substrate, the enzyme activity was measured as follows. 8.32 U/mL was analyzed in the wild type strain, 19.15 U/mL in the G3-1 mutant, 4.31 U/mL in the F12-1 mutant, and 0.54 U/mL in the F63-1 mutant. As for the ammonia-specific 5'-XMP mutants, their enzyme activities were found to be 0.21 U/mL for G1C, 0.16 U/mL for G3C, 0.24 U/mL for F12C, and 0.40 U/mL for F63C.

Figure 17:
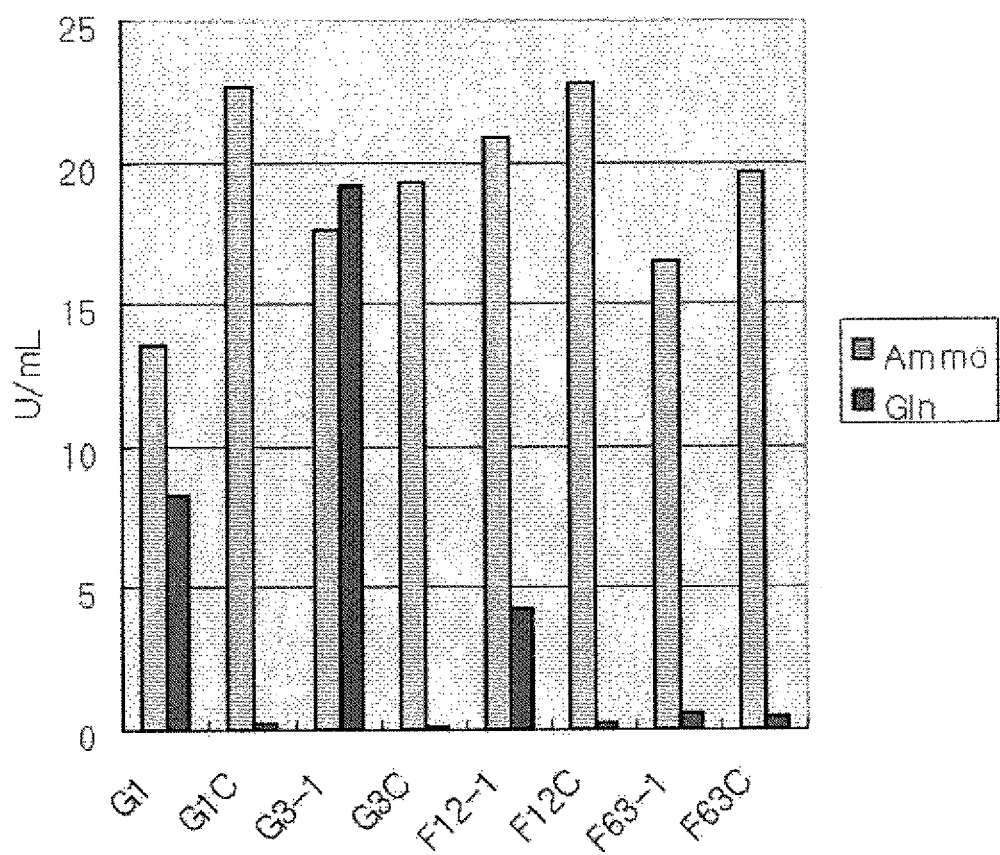
FIG. 17 is a graph showing activities per unit of a wild type 5'-XMP aminase (G1) derived from E. coli, 5'-XMP mutants (G3-1, F12-1, F63-1) prepared through random mutagenesis, and ammonia-specific mutants (G1C, G3C, F12C, F63C) in culture media containing ammonia or L-glutamine as a substrate, wherein Ammo stands for ammonia and Gln stands for glutamine.

As is apparent from the above data, the ammonia-specific 5'-XMP aminase mutants are almost inactive in converting 5'-XMP to 5'-GMP when using L-glutamine as a substrate, but are found to have about 1.4- to 1.7-fold higher activity in the conversion of 5'-XMP to 5'-GMP in the presence of ammonia than the corresponding wild-type or random mutants (FIG. 17).

EXAMPLE 7

Intracellular Stability of Expression Vectors for Ammonia-Specific 5'-XMP Aminase Mutants In order to compare the expression vectors of the ammonia-specific 5'-XMP aminase mutants with regard to intracellular stability, the expression vectors remaining after cultivation were quantitatively measured.

After the completion of cultivation, the culture fluid was diluted to $10^{-5}$ its original concentration and was smeared onto LB plates (Bacto-Trypton 1%, Yeast extract 1%, NaCl 0.5%) containing either 50 g/mL of kanamycin or no antibiotics. Incubation at 30° C. for 16 hrs was followed by counting the number of colonies formed. The numbers of colonies were expressed as percentages of the control, and the results are depicted in FIG. 18.

Figure 18:
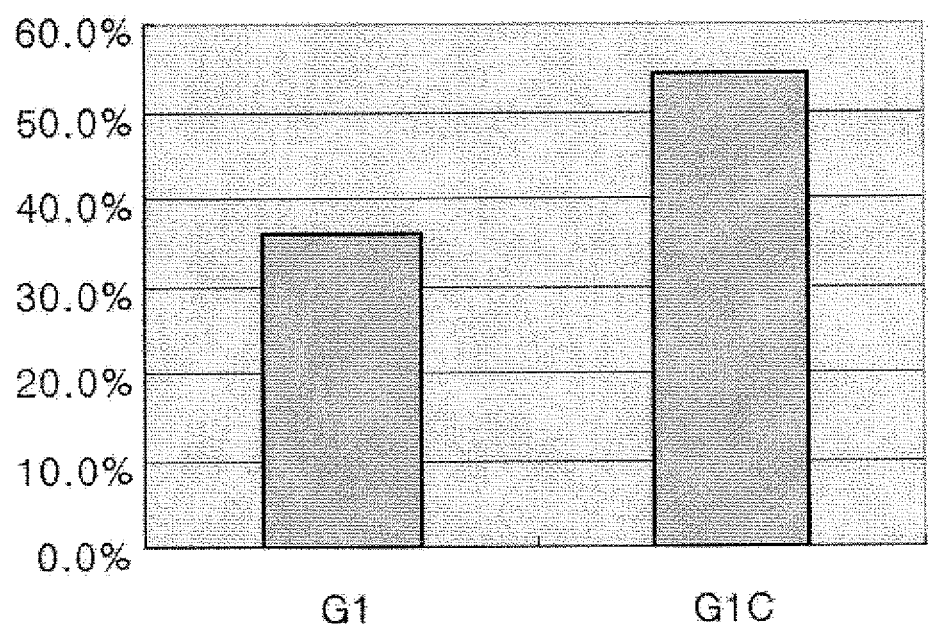
FIG. 18 is a graph comparing intracellular stability between an expression vector carrying a gene (G1) encoding wild-type 5'-XMP aminase and an expression vector carrying a gene (G1C) encoding an ammonia-specific 5'-XMP aminase, in which the cysteine residue at position 86 of the gene G1 is substituted with alanine.

As seen in FIG. 18, the number of colonies in which the expression vector carrying the gene encoding the G1C ammonia-specific 5'-XMP aminase mutant is contained amounted to 54.3% of the control, while in the case of the wild-type 5'-XMP aminase, the number is no greater than 36.0%. These data indicate that the expression vector carrying a gene encoding ammonia-specific 5'-XMP aminase is more stable within the cell, thus enhancing the catalytic activity.

INDUSTRIAL APPLICABILITY

As described and demonstrated hereinbefore, in order to effectively produce 5'-GMP useful as a flavor enhancer, the present invention provides ammonia-specific 5'-XMP aminase mutants by imparting ammonia specificity to wild-type 5'-XMP aminase and randomly mutated 5'-XMP aminase mutants having enhanced activity, along with a preparation method thereof. Besides having enhanced activity relative to the native form, the ammonia-specific 5'-XMP aminase mutants of the present invention are useful in a biological process for producing 5'-GMP because they can be stably maintained within cells due to their low cytotoxicity.

---

The invention claimed is:

1. An ammonia-specific 5'-XMP aminase mutant produced by substituting an alanine for the cysteine at position 86 of the 5'-XMP aminase set forth in SEQ ID NO:4, 6, 8, 10, 12, or 14.

2. The ammonia-specific 5'-XMP aminase mutant of claim 1, having an amino acid sequence represented by SEQ ID NO:18, 20 or 22.

3. A nucleic acid molecule coding for the ammonia-specific 5'-XMP aminase mutant of claim 1.

4. An expression vector carrying the nucleic acid molecule of claim 3.

5. A prokaryotic transformant, transformed with the expression vector of claim 4.

6. A method for converting 5'-XMP into 5'-GMP, comprising converting 5'-XMP into 5'-GMP using the ammonia-specific 5'-XMP aminase mutant of claim 1.

7. A method for producing an ammonia-specific 5'-XMP aminase mutant, comprising substituting an alanine for the cysteine residue at position 86 of the amino acid sequence set forth in SEQ ID NO:4, 6, 8, 10, 12, or 14, whereby the ammonia-specific 5'-XMP aminase mutant is substantially inactive to glutamine, but reacts specifically with ammonia to convert 5'-XMP into 5'-GMP at enhanced efficiency.

8. A method for converting 5'-XMP into 5'-GMP, comprising converting 5'-XMP into 5'-GMP using the ammonia-specific 5'-XMP aminase mutant of claim 2.

* * * * *

UNITED STATES PATENT AND TRADEMARK OFFICE
CERTIFICATE OF CORRECTION

| | | |
|---|---|---|
| PATENT NO. | : 8,669,078 B2 | Page 1 of 1 |
| APPLICATION NO. | : 12/097104 | |
| DATED | : March 11, 2014 | |
| INVENTOR(S) | : Pan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1191 days.

Signed and Sealed this
Seventh Day of July, 2015

Michelle K. Lee
*Director of the United States Patent and Trademark Office*

SEQUENCE LISTING

```
<160> NUMBER OF SEQ ID NOS: 28

<210> SEQ ID NO 1
<211> LENGTH: 1578
<212> TYPE: DNA
<213> ORGANISM: Escherichia coli K12
<220> FEATURE:
<221> NAME/KEY: gene
<222> LOCATION: (1)...(1578)
<220> FEATURE:
<221> NAME/KEY: CDS
<222> LOCATION: (1)...(1575)

<400> SEQUENCE: 1 atg acg gaa aac att cat aag cat cgc atc ctc att ctg gac ttc ggt       48
Met Thr Glu Asn Ile His Lys His Arg Ile Leu Ile Leu Asp Phe Gly
 1               5                  10                  15 tct cag tac act caa ctg gtt gcg cgc cgc gtg cgt gag ctg ggt gtt       96
Ser Gln Tyr Thr Gln Leu Val Ala Arg Arg Val Arg Glu Leu Gly Val
             20                  25                  30 tac tgc gaa ctg tgg gcg tgg gat gtg aca gaa gca caa att cgt gac      144
Tyr Cys Glu Leu Trp Ala Trp Asp Val Thr Glu Ala Gln Ile Arg Asp
         35                  40                  45 ttc aat cca agc ggc att att ctt tcc ggc ggc ccg gaa agt act act      192
Phe Asn Pro Ser Gly Ile Ile Leu Ser Gly Gly Pro Glu Ser Thr Thr
     50                  55                  60 gaa gaa aac agt ccg cgt gcg ccg cag tat gtc ttt gaa gca ggc gta      240
Glu Glu Asn Ser Pro Arg Ala Pro Gln Tyr Val Phe Glu Ala Gly Val
 65                  70                  75                  80 ccg gta ttc ggc gtt tgc tat ggc atg cag acc atg gca atg cag ttg      288
Pro Val Phe Gly Val Cys Tyr Gly Met Gln Thr Met Ala Met Gln Leu
                 85                  90                  95 ggc ggt cac gtt gaa gcc tct aac gaa cgt gaa ttt ggc tac gcg cag      336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg      384
Val Glu Val Val Asn Asp Ser Ala Leu Val Arg Gly Ile Glu Asp Ala
        115                 120                 125 ctg acc gca gac ggt aaa ccg ctc ctc gat gtc tgg atg agc cac ggc      432
Leu Thr Ala Asp Gly Lys Pro Leu Leu Asp Val Trp Met Ser His Gly
    130                 135                 140
```

```
gat aaa gtt acc gct att ccg tcc gac ttc atc acc gta gcc agc acc    480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat    528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt atg cgc    576
Gly Val Gln Phe His Pro Glu Val Thr His Thr Arg Gln Gly Met Arg
            180                 185                 190 atg ctg gag cgt ttt gtg cgt gat atc tgc cag tgt gaa gcc ctg tgg    624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag    672
Thr Pro Ala Lys Ile Ile Asp Asp Ala Val Ala Arg Ile Arg Glu Gln
    210                 215                 220 gta ggc gac gat aaa gtc atc ctc ggc ctc tct ggt ggt gtg gat tcc    720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act    768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag    816
Cys Val Phe Val Asp Asn Gly Leu Leu Arg Leu Asn Glu Ala Glu Gln
                260                 265                 270 gtt ctg gat atg ttt ggc gat cac ttt ggt ctt aac att gtt cac gta    864
Val Leu Asp Met Phe Gly Asp His Phe Gly Leu Asn Ile Val His Val
        275                 280                 285 ccg gca gaa gat cgc ttc ctg tca gcg ctg gct ggc gaa aac gat ccg    912
Pro Ala Glu Asp Arg Phe Leu Ser Ala Leu Ala Gly Glu Asn Asp Pro
    290                 295                 300 gaa gca aaa cgt aaa atc atc ggt cgc gtt ttc gtt gaa gta ttc gat    960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc   1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca   1056
Ile Tyr Pro Asp Val Ile Glu Ser Ala Ala Ser Ala Thr Gly Lys Ala
                340                 345                 350 cac gtc atc aaa tct cac cac aac gtg ggc ggc ctg ccg aaa gag atg   1104
His Val Ile Lys Ser His His Asn Val Gly Gly Leu Pro Lys Glu Met
            355                 360                 365 aag atg ggc ctg gtt gaa ccg ctg aaa gag ctg ttc aaa gac gaa gtg   1152
Lys Met Gly Leu Val Glu Pro Leu Lys Glu Leu Phe Lys Asp Glu Val
        370                 375                 380 cgt aag att ggt ctg gag ctg ggc ctg ccg tac gac atg ctg tac cgt   1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg   1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att   1296
Lys Lys Glu Tyr Cys Asp Leu Leu Arg Arg Ala Asp Ala Ile Phe Ile
                420                 425                 430 gaa gaa ctg cgt aaa gcg gac ctg tac gac aaa gtc agc cag gcg ttc   1344
Glu Glu Leu Arg Lys Ala Asp Leu Tyr Asp Lys Val Ser Gln Ala Phe
            435                 440                 445 act gtg ttc ctg ccg gta cgt tcc gtt ggc gta atg ggc gat ggt cgt   1392
Thr Val Phe Leu Pro Val Arg Ser Val Gly Val Met Gly Asp Gly Arg
    450                 455                 460
```

| | | | | | | | | | | | | | |
|---|---|---|---|---|---|---|---|---|---|---|---|---|---|
| aag | tat | gac | tgg | gtt | gtc | tct | ctg | cgt | gct | gtc | gaa | acc | atc | gac | ttt | 1440 |
| Lys | Tyr | Asp | Trp | Val | Val | Ser | Leu | Arg | Ala | Val | Glu | Thr | Ile | Asp | Phe | |
| 465 | | | | 470 | | | | | 475 | | | | | 480 | | |

```
aag tat gac tgg gtt gtc tct ctg cgt gct gtc gaa acc atc gac ttt      1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt      1488
Met Thr Ala His Trp Ala His Leu Pro Tyr Asp Phe Leu Gly Arg Val
                    485                 490                 495 tcc aac cgc att atc aat gaa gtg aac ggt att tcc cgc gtg gtg tat      1536
Ser Asn Arg Ile Ile Asn Glu Val Asn Gly Ile Ser Arg Val Val Tyr
                500                 505                 510 gac atc agc ggc aag ccg cca gct acc att gag tgg gaa tga              1578
Asp Ile Ser Gly Lys Pro Pro Ala Thr Ile Glu Trp Glu
            515                 520                 525

<210> SEQ ID NO 2
<211> LENGTH: 525
<212> TYPE: PRT
<213> ORGANISM: Escherichia coli K12

<400> SEQUENCE: 2

Met Thr Glu Asn Ile His Lys His Arg Ile Leu Ile Leu Asp Phe Gly
 1               5                  10                  15

Ser Gln Tyr Thr Gln Leu Val Ala Arg Val Arg Glu Leu Gly Val
                20                  25                  30

Tyr Cys Glu Leu Trp Ala Trp Asp Val Thr Glu Ala Gln Ile Arg Asp
            35                  40                  45

Phe Asn Pro Ser Gly Ile Ile Leu Ser Gly Gly Pro Glu Ser Thr Thr
 50                  55                  60

Glu Glu Asn Ser Pro Arg Ala Pro Gln Tyr Val Phe Glu Ala Gly Val
65                  70                  75                  80

Pro Val Phe Gly Val Cys Tyr Gly Met Gln Thr Met Ala Met Gln Leu
                85                  90                  95

Gly Gly His Val Glu Ala Ser Asn Glu Arg Glu Phe Gly Tyr Ala Gln
                100                 105                 110

Val Glu Val Val Asn Asp Ser Ala Leu Val Arg Gly Ile Glu Asp Ala
            115                 120                 125

Leu Thr Ala Asp Gly Lys Pro Leu Leu Asp Val Trp Met Ser His Gly
130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Glu Lys Arg Phe Tyr
                165                 170                 175

Gly Val Gln Phe His Pro Glu Val Thr His Thr Arg Gln Gly Met Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
290                 295                 300
```

```
Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
            325                 330                 335

Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
            355                 360                 365

Lys Met Gly Leu Val Glu Pro Leu Lys Glu Leu Phe Lys Asp Glu Val
            370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
            435                 440                 445

Thr Val Phe Leu Pro Val Arg Ser Val Gly Val Met Gly Asp Gly Arg
450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
            515                 520                 525

<210> SEQ ID NO 3
<211> LENGTH: 1578
<212> TYPE: DNA
<213> ORGANISM: Artificial Sequence
<220> FEATURE:
<223> OTHER INFORMATION: DNA sequence of mutant G3
<220> FEATURE:
<221> NAME/KEY: CDS
<222> LOCATION: (1)..(1575)
<223> OTHER INFORMATION: amino acid sequence of XMP aminase mutant G3

<400> SEQUENCE: 3 atg acg gaa aac att cat aag cat cgc atc ctc att ctg gac ttc ggt         48
Met Thr Glu Asn Ile His Lys His Arg Ile Leu Ile Leu Asp Phe Gly
1               5                   10                  15 tct cag tac act caa ctg gtt gcg cgc cgc gtg cgt gag ctg ggt gtt         96
Ser Gln Tyr Thr Gln Leu Val Ala Arg Arg Val Arg Glu Leu Gly Val
                20                  25                  30 tac tgc gaa ctg tgg gcg tgg gat gtg aca gaa gca caa att cgt gac        144
Tyr Cys Glu Leu Trp Ala Trp Asp Val Thr Glu Ala Gln Ile Arg Asp
            35                  40                  45 ttc aat cca tgc ggc att att ctt tcc ggc ggc ccg gaa agt act act        192
Phe Asn Pro Cys Gly Ile Ile Leu Ser Gly Gly Pro Glu Ser Thr Thr
        50                  55                  60 gaa gaa aac agt ccg cgt gcg ccg cag tat gtc ttt gaa gca ggc gta        240
Glu Glu Asn Ser Pro Arg Ala Pro Gln Tyr Val Phe Glu Ala Gly Val
65                  70                  75                  80 ccg gta ttc ggc gtt tgc tat ggc atg cag acc atg gca atg cag ttg        288
Pro Val Phe Gly Val Cys Tyr Gly Met Gln Thr Met Ala Met Gln Leu
                85                  90                  95
```

| | | | | | | | | | | | | | | | | |
|---|---|---|---|---|---|---|---|---|---|---|---|---|---|---|---|---|
| ggc | ggt | cac | gtt | gaa | gcc | tct | aac | gaa | cgt | gaa | ttt | ggc | tac | gcg | cag | 336 |
| Gly | Gly | His | Val | Glu | Ala | Ser | Asn | Glu | Arg | Glu | Phe | Gly | Tyr | Ala | Gln | |
| | | | 100 | | | | 105 | | | | | 110 | | | | |
| gtt | gaa | gtc | gta | aac | gac | agc | gca | ctg | gtt | cgc | ggt | atc | gaa | gat | gcg | 384 |
| Val | Glu | Val | Val | Asn | Asp | Ser | Ala | Leu | Val | Arg | Gly | Ile | Glu | Asp | Ala | |
| | | | | 115 | | | | 120 | | | | 125 | | | | |
| ctg | acc | gca | gac | ggt | aaa | ccg | ctg | ctc | gat | gtc | tgg | atg | agc | cac | ggc | 432 |
| Leu | Thr | Ala | Asp | Gly | Lys | Pro | Leu | Leu | Asp | Val | Trp | Met | Ser | His | Gly | |
| | 130 | | | | | 135 | | | | | 140 | | | | | |
| gat | aaa | gtt | acc | gct | att | ccg | tcc | gac | ttc | atc | acc | gta | gcc | agc | acc | 480 |
| Asp | Lys | Val | Thr | Ala | Ile | Pro | Ser | Asp | Phe | Ile | Thr | Val | Ala | Ser | Thr | |
| 145 | | | | | 150 | | | | | 155 | | | | | 160 | |
| gaa | agc | tgc | ccg | ttt | gcc | att | atg | gct | aac | gaa | gaa | aaa | cgc | ttc | tat | 528 |
| Glu | Ser | Cys | Pro | Phe | Ala | Ile | Met | Ala | Asn | Glu | Glu | Lys | Arg | Phe | Tyr | |
| | | | 165 | | | | | 170 | | | | | 175 | | | |
| ggc | gta | cag | ttc | cac | ccg | gaa | gtg | act | cat | acc | cgc | cag | ggt | acg | cgc | 576 |
| Gly | Val | Gln | Phe | His | Pro | Glu | Val | Thr | His | Thr | Arg | Gln | Gly | Thr | Arg | |
| | | | 180 | | | | | 185 | | | | | 190 | | | |
| atg | ctg | gag | cgt | ttt | gtg | cgt | gat | atc | tgc | cag | tgt | gaa | gcc | ctg | tgg | 624 |
| Met | Leu | Glu | Arg | Phe | Val | Arg | Asp | Ile | Cys | Gln | Cys | Glu | Ala | Leu | Trp | |
| | | 195 | | | | | 200 | | | | | 205 | | | | |
| acg | cca | gcg | aaa | att | atc | gac | gat | gct | gta | gct | cgc | atc | cgc | gag | cag | 672 |
| Thr | Pro | Ala | Lys | Ile | Ile | Asp | Asp | Ala | Val | Ala | Arg | Ile | Arg | Glu | Gln | |
| | 210 | | | | | 215 | | | | | 220 | | | | | |
| gta | ggc | gac | gat | aaa | gtc | atc | ctc | ggc | ctc | tct | ggt | ggt | gtg | gat | tcc | 720 |
| Val | Gly | Asp | Asp | Lys | Val | Ile | Leu | Gly | Leu | Ser | Gly | Gly | Val | Asp | Ser | |
| 225 | | | | | 230 | | | | | 235 | | | | | 240 | |
| tcc | gta | acc | gca | atg | ctg | ctg | cac | cgc | gct | atc | ggt | aaa | aac | ctg | act | 768 |
| Ser | Val | Thr | Ala | Met | Leu | Leu | His | Arg | Ala | Ile | Gly | Lys | Asn | Leu | Thr | |
| | | | | | 245 | | | | | 250 | | | | | 255 | |
| tgc | gta | ttc | gtc | gac | aac | ggc | ctg | ctg | cgc | ctc | aac | gaa | gca | gag | cag | 816 |
| Cys | Val | Phe | Val | Asp | Asn | Gly | Leu | Leu | Arg | Leu | Asn | Glu | Ala | Glu | Gln | |
| | | | 260 | | | | | 265 | | | | | 270 | | | |
| gtt | ctg | gat | atg | ttt | ggc | gat | cac | ttt | ggt | ctt | aac | att | gtt | cac | gta | 864 |
| Val | Leu | Asp | Met | Phe | Gly | Asp | His | Phe | Gly | Leu | Asn | Ile | Val | His | Val | |
| | | 275 | | | | | 280 | | | | | 285 | | | | |
| ccg | gca | gaa | gat | cgc | ttc | ctg | tca | gcg | ctg | gct | ggc | gaa | aac | gat | ccg | 912 |
| Pro | Ala | Glu | Asp | Arg | Phe | Leu | Ser | Ala | Leu | Ala | Gly | Glu | Asn | Asp | Pro | |
| | 290 | | | | | 295 | | | | | 300 | | | | | |
| gaa | gca | aaa | cgt | aaa | atc | atc | ggt | cgc | gtt | ttc | gtt | gaa | gta | ttc | gat | 960 |
| Glu | Ala | Lys | Arg | Lys | Ile | Ile | Gly | Arg | Val | Phe | Val | Glu | Val | Phe | Asp | |
| 305 | | | | | 310 | | | | | 315 | | | | | 320 | |
| gaa | gaa | gcg | ctg | aaa | ctg | gaa | gac | gtg | aag | tgg | ctg | gcg | cag | ggc | acc | 1008 |
| Glu | Glu | Ala | Leu | Lys | Leu | Glu | Asp | Val | Lys | Trp | Leu | Ala | Gln | Gly | Thr | |
| | | | | 325 | | | | | 330 | | | | | 335 | | |
| atc | tac | cct | gac | gtt | atc | gaa | tct | gcg | gcg | tct | gca | acc | ggt | aaa | gca | 1056 |
| Ile | Tyr | Pro | Asp | Val | Ile | Glu | Ser | Ala | Ala | Ser | Ala | Thr | Gly | Lys | Ala | |
| | | | 340 | | | | | 345 | | | | | 350 | | | |
| cac | gtc | atc | aaa | tct | cac | cac | aac | gtg | ggc | ggc | ctg | ccg | aaa | gag | atg | 1104 |
| His | Val | Ile | Lys | Ser | His | His | Asn | Val | Gly | Gly | Leu | Pro | Lys | Glu | Met | |
| | | | 355 | | | | | 360 | | | | | 365 | | | |
| aag | atg | ggc | ctg | gtt | gaa | ccg | ctg | aaa | gag | ctg | ttc | aaa | gac | gaa | gtg | 1152 |
| Lys | Met | Gly | Leu | Val | Glu | Pro | Leu | Lys | Glu | Leu | Phe | Lys | Asp | Glu | Val | |
| | 370 | | | | | 375 | | | | | 380 | | | | | |
| cgt | aag | att | ggt | ctg | gag | ctg | ggc | ctg | ccg | tac | gac | atg | ctg | tac | cgt | 1200 |
| Arg | Lys | Ile | Gly | Leu | Glu | Leu | Gly | Leu | Pro | Tyr | Asp | Met | Leu | Tyr | Arg | |
| 385 | | | | | 390 | | | | | 395 | | | | | 400 | |
| cac | ccg | ttc | ccg | gga | cca | ggc | ctt | ggc | gtt | cgt | gtt | ctg | ggt | gaa | gtg | 1248 |
| His | Pro | Phe | Pro | Gly | Pro | Gly | Leu | Gly | Val | Arg | Val | Leu | Gly | Glu | Val | |
| | | | | 405 | | | | | 410 | | | | | 415 | | |

```
aag aaa gag tac tgt gac ctg ctg cgc cgt gct gac gcc atc ttc att       1296
Lys Lys Glu Tyr Cys Asp Leu Leu Arg Arg Ala Asp Ala Ile Phe Ile
        420                 425                 430 gaa gaa ctg cgt aaa gcg gac ctg tac gac aaa gtc agc cag gcg ttc       1344
Glu Glu Leu Arg Lys Ala Asp Leu Tyr Asp Lys Val Ser Gln Ala Phe
        435                 440                 445 act gtg ttc ctg ccg gta cgt tcc gtt ggc gta atg ggc gat ggt cgt       1392
Thr Val Phe Leu Pro Val Arg Ser Val Gly Val Met Gly Asp Gly Arg
450                 455                 460 aag tat gac tgg gtt gtc tct ctg cgt gct gtc gaa acc atc gac ttt       1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt       1488
Met Thr Ala His Trp Ala His Leu Pro Tyr Asp Phe Leu Gly Arg Val
            485                 490                 495 tcc aac cgc att atc aat gaa gtg aac ggt att tcc cgc gtg gtg tat       1536
Ser Asn Arg Ile Ile Asn Glu Val Asn Gly Ile Ser Arg Val Val Tyr
                500                 505                 510 gac atc agc ggc aag ccg cca gct acc att gag tgg gaa tga                1578
Asp Ile Ser Gly Lys Pro Pro Ala Thr Ile Glu Trp Glu
            515                 520                 525

<210> SEQ ID NO 4
<211> LENGTH: 525
<212> TYPE: PRT
<213> ORGANISM: ARtificial Sequence
<220> FEATURE:
<223> OTHER INFORMATION: amino acid sequence of XMP aminase mutant G3

<400> SEQUENCE: 4

Met Thr Glu Asn Ile His Lys His Arg Ile Leu Ile Leu Asp Phe Gly
 1               5                  10                  15

Ser Gln Tyr Thr Gln Leu Val Ala Arg Arg Val Arg Glu Leu Gly Val
            20                  25                  30

Tyr Cys Glu Leu Trp Ala Trp Asp Val Thr Glu Ala Gln Ile Arg Asp
        35                  40                  45

Phe Asn Pro Cys Gly Ile Ile Leu Ser Gly Gly Pro Glu Ser Thr Thr
    50                  55                  60

Glu Glu Asn Ser Pro Arg Ala Pro Gln Tyr Val Phe Glu Ala Gly Val
65                  70                  75                  80

Pro Val Phe Gly Val Cys Tyr Gly Met Gln Thr Met Ala Met Gln Leu
                85                  90                  95

Gly Gly His Val Glu Ala Ser Asn Glu Arg Glu Phe Gly Tyr Ala Gln
            100                 105                 110

Val Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
    130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Glu Lys Arg Phe Tyr
                165                 170                 175

Gly Val Gln Phe His Pro Glu Val Thr His Thr Arg Gln Gly Thr Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
    210                 215                 220
```

```
Val Gly Asp Asp Lys Val Ile Leu Gly Leu Ser Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
    290                 295                 300

Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
                325                 330                 335

Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
        355                 360                 365

Lys Met Gly Leu Val Glu Pro Leu Lys Glu Leu Phe Lys Asp Glu Val
370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
        435                 440                 445

Thr Val Phe Leu Pro Val Arg Ser Val Gly Val Met Gly Asp Gly Arg
    450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
        515                 520                 525

<210> SEQ ID NO 5
<211> LENGTH: 1578
<212> TYPE: DNA
<213> ORGANISM: Artificial Sequence
<220> FEATURE:
<223> OTHER INFORMATION: DNA sequence of XMP aminase mutant F12
<220> FEATURE:
<221> NAME/KEY: CDS
<222> LOCATION: (1)..(1575)
<223> OTHER INFORMATION: amino acid sequence of XMP aminase mutnat F12

<400> SEQUENCE: 5 atg acg gaa aac att cat aag cat cgc atc ctc att ctg gac ttc ggt      48
Met Thr Glu Asn Ile His Lys His Arg Ile Leu Ile Leu Asp Phe Gly
  1               5                  10                  15 tct cag tac act caa ctg gtt gcg cgc cgc gtg cgt gag ctg ggt gtt      96
Ser Gln Tyr Thr Gln Leu Val Ala Arg Arg Val Arg Glu Leu Gly Val
             20                  25                  30
```

-continued

| | | |
|---|---|---|
| tac tgc gaa ctg tgg gcg tgg gat gtg aca gaa gca caa att cgt gac<br>Tyr Cys Glu Leu Trp Ala Trp Asp Val Thr Glu Ala Gln Ile Arg Asp<br>           35                    40                   45 | 144 |

```
tac tgc gaa ctg tgg gcg tgg gat gtg aca gaa gca caa att cgt gac      144
Tyr Cys Glu Leu Trp Ala Trp Asp Val Thr Glu Ala Gln Ile Arg Asp
         35                  40                  45 ttc aat cca agc ggc att att ctt tcc ggc ggc ccg gaa agt act act      192
Phe Asn Pro Ser Gly Ile Ile Leu Ser Gly Gly Pro Glu Ser Thr Thr
 50                  55                  60 gaa gaa aac agt ccg cgt gcg ccg cag tat gtc ttt gaa gca ggc gta      240
Glu Glu Asn Ser Pro Arg Ala Pro Gln Tyr Val Phe Glu Ala Gly Val
 65                  70                  75                  80 ccg gta ttc ggc gtt tgc tat ggc atg cag acc atg gta atg cag ttg      288
Pro Val Phe Gly Val Cys Tyr Gly Met Gln Thr Met Val Met Gln Leu
                 85                  90                  95 ggc ggt cac gtt gaa gcc tct aac gaa cgt gaa ttt ggc tac gcg cag      336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg      384
Val Glu Val Val Asn Asp Ser Ala Leu Val Arg Gly Ile Glu Asp Ala
        115                 120                 125 ctg acc gca gac ggt aaa ccg ctg ctc gat gtc tgg atg agc cac ggc      432
Leu Thr Ala Asp Gly Lys Pro Leu Leu Asp Val Trp Met Ser His Gly
130                 135                 140 gat aaa gtt acc gct att ccg ccc gac ttc atc acc gta gcc agc acc      480
Asp Lys Val Thr Ala Ile Pro Pro Asp Phe Ile Thr Val Ala Ser Thr
145                 150                 155                 160 gaa agc tgc ccg ttt gcc att atg gct aac gaa gaa aaa cgc ttc tat      528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt atg cgc      576
Gly Val Gln Phe His Pro Glu Val Thr His Thr Arg Gln Gly Met Arg
            180                 185                 190 atg ctg gag cgt ttt gtg cgt gat atc tgc cag tgt gaa gcc ctg tgg      624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag      672
Thr Pro Ala Lys Ile Ile Asp Asp Ala Val Ala Arg Ile Arg Glu Gln
210                 215                 220 gta ggc gac gat aaa gtc atc ctc ggc ctc tct ggt ggt gtg gat tcc      720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act      768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag      816
Cys Val Phe Val Asp Asn Gly Leu Leu Arg Leu Asn Glu Ala Glu Gln
            260                 265                 270 gtt ctg gat atg ttt ggc gat cac ttt ggt ctt aac att gtt cac gta      864
Val Leu Asp Met Phe Gly Asp His Phe Gly Leu Asn Ile Val His Val
        275                 280                 285 ccg gca gaa gat cgc ttc ctg tca gcg ctg gct ggc gaa aac gat ccg      912
Pro Ala Glu Asp Arg Phe Leu Ser Ala Leu Ala Gly Glu Asn Asp Pro
290                 295                 300 gaa gca aaa cgt aaa atc atc ggt cgc gtt ttc gtt gaa gta ttc gat      960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc     1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca     1056
Ile Tyr Pro Asp Val Ile Glu Ser Ala Ala Ser Ala Thr Gly Lys Ala
            340                 345                 350
```

```
cac gtc atc aaa tct cac cac aac gtg ggc ggc ctg ccg aaa gag atg        1104
His Val Ile Lys Ser His His Asn Val Gly Gly Leu Pro Lys Glu Met
            355                 360                 365 aag atg ggc ctg gtt gaa ccg ctg aaa gag ctg ttc aaa gac gaa gtg        1152
Lys Met Gly Leu Val Glu Pro Leu Lys Glu Leu Phe Lys Asp Glu Val
    370                 375                 380 cgt aag att ggt ctg gag ctg ggc ctg ccg tac gac atg ctg tac cgt        1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg        1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att        1296
Lys Lys Glu Tyr Cys Asp Leu Leu Arg Arg Ala Asp Ala Ile Phe Ile
            420                 425                 430 gaa gaa ctg cgt aaa gcg gac ctg tac gac aaa gtc agc cag gcg ttc        1344
Glu Glu Leu Arg Lys Ala Asp Leu Tyr Asp Lys Val Ser Gln Ala Phe
        435                 440                 445 act gtg ttc ctg ccg gta cgt tcc gtt ggc gta atg ggc gat ggt cgt        1392
Thr Val Phe Leu Pro Val Arg Ser Val Gly Val Met Gly Asp Gly Arg
    450                 455                 460 aag tat gac tgg gtt gtc tct ctg cgt gct gtc gaa acc atc gac ttt        1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt        1488
Met Thr Ala His Trp Ala His Leu Pro Tyr Asp Phe Leu Gly Arg Val
                485                 490                 495 tcc aac cgc att atc aat gaa gtg aac ggt att tcc cgc gtg gtg tat        1536
Ser Asn Arg Ile Ile Asn Glu Val Asn Gly Ile Ser Arg Val Val Tyr
            500                 505                 510 gac atc agc ggc aag ccg cca gct acc att gag tgg gaa tga              1578
Asp Ile Ser Gly Lys Pro Pro Ala Thr Ile Glu Trp Glu
        515                 520                 525

<210> SEQ ID NO 6
<211> LENGTH: 525
<212> TYPE: PRT
<213> ORGANISM: Artificial Sequence
<220> FEATURE:
<223> OTHER INFORMATION: amino acid sequence of XMP aminase mutant F12

<400> SEQUENCE: 6

Met Thr Glu Asn Ile His Lys His Arg Ile Leu Ile Leu Asp Phe Gly
  1               5                  10                  15

Ser Gln Tyr Thr Gln Leu Val Ala Arg Arg Val Arg Glu Leu Gly Val
                 20                  25                  30

Tyr Cys Glu Leu Trp Ala Trp Asp Val Thr Glu Ala Gln Ile Arg Asp
             35                  40                  45

Phe Asn Pro Ser Gly Ile Ile Leu Ser Gly Gly Pro Glu Ser Thr Thr
     50                  55                  60

Glu Glu Asn Ser Pro Arg Ala Pro Gln Tyr Val Phe Glu Ala Gly Val
 65                  70                  75                  80

Pro Val Phe Gly Val Cys Tyr Gly Met Gln Thr Met Val Met Gln Leu
                 85                  90                  95

Gly Gly His Val Glu Ala Ser Asn Glu Arg Glu Phe Gly Tyr Ala Gln
            100                 105                 110

Val Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
    130                 135                 140
```

Asp Lys Val Thr Ala Ile Pro Pro Asp Phe Ile Thr Val Ala Ser Thr
145                 150                 155                 160

Glu Ser Cys Pro Phe Ala Ile Met Ala Asn Glu Glu Lys Arg Phe Tyr
                165                 170                 175

Gly Val Gln Phe His Pro Glu Val Thr His Thr Arg Gln Gly Met Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
    210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
    290                 295                 300

Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
                325                 330                 335

Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
        355                 360                 365

Lys Met Gly Leu Val Glu Pro Leu Lys Glu Leu Phe Lys Asp Glu Val
    370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
        435                 440                 445

Thr Val Phe Leu Pro Val Arg Ser Val Gly Val Met Gly Asp Gly Arg
    450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
        515                 520                 525

<210> SEQ ID NO 7
<211> LENGTH: 1578
<212> TYPE: DNA
<213> ORGANISM: Artificial Sequence
<220> FEATURE:
<223> OTHER INFORMATION: DNA sequence of XMP aminase mutant F63

```
<220> FEATURE:
<221> NAME/KEY: CDS
<222> LOCATION: (1)..(1575)
<223> OTHER INFORMATION: amino acid sequence of XMP aminase mutant F63

<400> SEQUENCE: 7 atg acg gaa aac att cat aag cat cgc atc ctc att ctg gac ttc ggt      48
Met Thr Glu Asn Ile His Lys His Arg Ile Leu Ile Leu Asp Phe Gly
 1               5                  10                  15 tct cag tac act caa ctg gtt gcg cgc cgt gtg cgt gag ctg ggt gtt     96
Ser Gln Tyr Thr Gln Leu Val Ala Arg Arg Val Arg Glu Leu Gly Val
             20                  25                  30 tac tgc gaa ctg tgg gcg tgg gat gtg aca gaa gca caa att cgt gac    144
Tyr Cys Glu Leu Trp Ala Trp Asp Val Thr Glu Ala Gln Ile Arg Asp
         35                  40                  45 ttc aat cca agc ggc att att ctt tcc ggc ggc ccg gaa agt act act    192
Phe Asn Pro Ser Gly Ile Ile Leu Ser Gly Gly Pro Glu Ser Thr Thr
     50                  55                  60 gaa gaa aac agt ccg cgt gcg ccg cag tat gtc ttt gaa gca ggc gta    240
Glu Glu Asn Ser Pro Arg Ala Pro Gln Tyr Val Phe Glu Ala Gly Val
 65                  70                  75                  80 ccg gta ttc ggc gtt tgc tat ggc atg cag acc atg gta atg cag ttg    288
Pro Val Phe Gly Val Cys Tyr Gly Met Gln Thr Met Val Met Gln Leu
                 85                  90                  95 ggc ggt cac gtt gaa gcc tct aac gaa cgt gaa ttt ggc tac gcg cag    336
Gly Gly His Val Glu Ala Ser Asn Glu Arg Glu Phe Gly Tyr Ala Gln
            100                 105                 110 gct gaa gtc gta aac gac agc gca ctg gtt cgc ggt atc gaa gat gcg    384
Ala Glu Val Val Asn Asp Ser Ala Leu Val Arg Gly Ile Glu Asp Ala
        115                 120                 125 ctg acc gca gac ggt aaa ccg ctg ctc gat gtc tgg atg agc cac ggc    432
Leu Thr Ala Asp Gly Lys Pro Leu Leu Asp Val Trp Met Ser His Gly
    130                 135                 140 gat aaa gtt acc gct att ccg tcc gac ttc atc acc gta gcc agc acc    480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat    528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt acg cgc    576
Gly Val Gln Phe His Pro Glu Val Thr His Thr Arg Gln Gly Thr Arg
            180                 185                 190 atg ctg gag cgt ttt gtg cgt gat atc tgc cag tgt gaa gcc ctg tgg    624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag    672
Thr Pro Ala Lys Ile Ile Asp Asp Ala Val Ala Arg Ile Arg Glu Gln
    210                 215                 220 gta ggc gac gat aaa gtc atc ctc ggc ctc tct ggt ggt gtg gat tcc    720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act    768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag    816
Cys Val Phe Val Asp Asn Gly Leu Leu Arg Leu Asn Glu Ala Glu Gln
            260                 265                 270 gtt ctg gat atg ttt ggc gat cac ttt ggt ctt aac att gtt cac gta    864
Val Leu Asp Met Phe Gly Asp His Phe Gly Leu Asn Ile Val His Val
        275                 280                 285 ccg gca gaa gat cgc ttc ctg tca gcg ctg gct ggc gaa aac gat ccg    912
```

| | | | | | | | | | | | | |
|---|---|---|---|---|---|---|---|---|---|---|---|---|
| Pro | Ala | Glu | Asp | Arg | Phe | Leu | Ser | Ala | Leu | Ala | Gly | Glu | Asn | Asp | Pro |
| | 290 | | | | 295 | | | | 300 | | | | | | |

```
gaa gca aaa cgt aaa atc atc ggt cgc gtt ttc gtt gaa gta ttc gat      960
Glu Ala Lys Arg Lys Ile Ile Gly Arg Val Phe Val Glu Val Phe Asp
305             310                 315                 320 gaa gaa gcg ctg aaa ctg gaa gac gtg aag tgg ctg gcg cag ggc acc     1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca     1056
Ile Tyr Pro Asp Val Ile Glu Ser Ala Ala Ser Ala Thr Gly Lys Ala
            340                 345                 350 cac gtc atc aaa tct cac cac aac gtg ggc ggc ctg ccg aaa gag atg     1104
His Val Ile Lys Ser His His Asn Val Gly Gly Leu Pro Lys Glu Met
        355                 360                 365 aag atg ggc ctg gtt gaa ccg ctg aaa gag ctg ttc aaa gac gaa gtg     1152
Lys Met Gly Leu Val Glu Pro Leu Lys Glu Leu Phe Lys Asp Glu Val
    370                 375                 380 cgt aag att ggt ctg gag ctg ggc ctg ccg tac gac atg ctg tac cgt     1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg     1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att     1296
Lys Lys Glu Tyr Cys Asp Leu Leu Arg Arg Ala Asp Ala Ile Phe Ile
            420                 425                 430 gaa gaa ctg cgt aaa gcg gac ctg tac gac aaa gtc agc cag gcg ttc     1344
Glu Glu Leu Arg Lys Ala Asp Leu Tyr Asp Lys Val Ser Gln Ala Phe
        435                 440                 445 act gtg ttc ctg ccg gta cgt tcc gtt ggc gta atg ggc gat ggt cgt     1392
Thr Val Phe Leu Pro Val Arg Ser Val Gly Val Met Gly Asp Gly Arg
    450                 455                 460 aag tat ggc tgg gtt gtc tct ctg cgt gct gtc gaa acc atc gac ttt     1440
Lys Tyr Gly Trp Val Val Ser Leu Arg Ala Val Glu Thr Ile Asp Phe
465                 470                 475                 480 atg acc gca cac tgg gcg cat ctg ccg tac gat ttc ctc ggt cgc gtt     1488
Met Thr Ala His Trp Ala His Leu Pro Tyr Asp Phe Leu Gly Arg Val
                485                 490                 495 tcc aac cgc att atc aat gaa gtg aac ggt att tcc cgc gtg gtg tat     1536
Ser Asn Arg Ile Ile Asn Glu Val Asn Gly Ile Ser Arg Val Val Tyr
            500                 505                 510 gac atc agc ggc aag ccg cca gct acc att gag tgg gaa tga             1578
Asp Ile Ser Gly Lys Pro Pro Ala Thr Ile Glu Trp Glu
        515                 520                 525

<210> SEQ ID NO 8
<211> LENGTH: 525
<212> TYPE: PRT
<213> ORGANISM: Artificial Sequence
<220> FEATURE:
<223> OTHER INFORMATION: amino acid sequence of XMP aminase mutant F63

<400> SEQUENCE: 8

Met Thr Glu Asn Ile His Lys His Arg Ile Leu Ile Leu Asp Phe Gly
 1               5                  10                  15

Ser Gln Tyr Thr Gln Leu Val Ala Arg Arg Val Arg Glu Leu Gly Val
                20                  25                  30

Tyr Cys Glu Leu Trp Ala Trp Asp Val Thr Glu Ala Gln Ile Arg Asp
            35                  40                  45

Phe Asn Pro Ser Gly Ile Ile Leu Ser Gly Gly Pro Glu Ser Thr Thr
        50                  55                  60
```

```
Glu Glu Asn Ser Pro Arg Ala Pro Gln Tyr Val Phe Glu Ala Gly Val
 65                  70                  75                  80

Pro Val Phe Gly Val Cys Tyr Gly Met Gln Thr Met Val Met Gln Leu
                 85                  90                  95

Gly Gly His Val Glu Ala Ser Asn Glu Arg Glu Phe Gly Tyr Ala Gln
            100                 105                 110

Ala Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
    130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Glu Lys Arg Phe Tyr
                165                 170                 175

Gly Val Gln Phe His Pro Glu Val Thr His Thr Arg Gln Gly Thr Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
    210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
    290                 295                 300

Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
                325                 330                 335

Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
        355                 360                 365

Lys Met Gly Leu Val Glu Pro Leu Lys Glu Leu Phe Lys Asp Glu Val
    370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
        435                 440                 445

Thr Val Phe Leu Pro Val Arg Ser Val Gly Val Met Gly Asp Gly Arg
    450                 455                 460

Lys Tyr Gly Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
```

```
                            485                 490                 495
Ser Asn Arg Ile Ile Asn Glu Val Asn Gly Ile Ser Arg Val Val Tyr
        500                 505                 510

Asp Ile Ser Gly Lys Pro Pro Ala Thr Ile Glu Trp Glu
        515                 520                 525

<210> SEQ ID NO 9
<211> LENGTH: 1578
<212> TYPE: DNA
<213> ORGANISM: Artificial Sequence
<220> FEATURE:
<223> OTHER INFORMATION: DNA sequence of G3-1
<220> FEATURE:
<221> NAME/KEY: CDS
<222> LOCATION: (1)..(1575)
<223> OTHER INFORMATION: Amino acid of G3-1

<400> SEQUENCE: 9 atg acg gaa aac att cat aag cat cgc atc ctc att ctg gac ttc ggt      48
Met Thr Glu Asn Ile His Lys His Arg Ile Leu Ile Leu Asp Phe Gly
 1               5                  10                  15 tct cag tac act caa ctg gtt gcg cgc cgc gtg cgt gag ctg ggt gtt      96
Ser Gln Tyr Thr Gln Leu Val Ala Arg Arg Val Arg Glu Leu Gly Val
            20                  25                  30 tac tgc gaa ttg tgg gcg tgg gat gtg aca gaa gca caa att cgt gac     144
Tyr Cys Glu Leu Trp Ala Trp Asp Val Thr Glu Ala Gln Ile Arg Asp
        35                  40                  45 ttc aat cca tgc ggc att att ctt tcc ggc ggc ccg gaa agt act act     192
Phe Asn Pro Cys Gly Ile Ile Leu Ser Gly Gly Pro Glu Ser Thr Thr
    50                  55                  60 gaa gaa aac agt ccg cgt gcg ccg cag tat gtc ttt gaa gca ggc gta     240
Glu Glu Asn Ser Pro Arg Ala Pro Gln Tyr Val Phe Glu Ala Gly Val
65                  70                  75                  80 ccg gta ttc ggc gtt tgc tat ggc atg cag acc atg gca atg cag ttg     288
Pro Val Phe Gly Val Cys Tyr Gly Met Gln Thr Met Ala Met Gln Leu
                85                  90                  95 ggc ggt cac gtt gaa gcc tct aac gaa cgt gaa ttt ggc tac gcg cag     336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg     384
Val Glu Val Val Asn Asp Ser Ala Leu Val Arg Gly Ile Glu Asp Ala
        115                 120                 125 ctg acc gca gac ggt aaa ccg ctg ctc gat gtc tgg atg agc cac ggc     432
Leu Thr Ala Asp Gly Lys Pro Leu Leu Asp Val Trp Met Ser His Gly
    130                 135                 140 gat aaa gtt acc gct att ccg tcc gac ttc atc acc gta gcc agc acc     480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat     528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt acg cgc     576
Gly Val Gln Phe His Pro Glu Val Thr His Thr Arg Gln Gly Thr Arg
            180                 185                 190 atg ctg gag cgt ttt gtg cgt gat atc tgc cag tgt gaa gcc ctg tgg     624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag     672
Thr Pro Ala Lys Ile Ile Asp Asp Ala Val Ala Arg Ile Arg Glu Gln
    210                 215                 220 gta ggc gac gat aaa gtc atc ctc ggc ctc tct ggt ggt gtg gat tcc     720
Val Gly Asp Asp Lys Val Ile Leu Gly Leu Ser Gly Gly Val Asp Ser
```

```
                225                 230                 235                 240
tcc gta acc gca atg ctg ctg cac cgc gct atc ggt aga aac ctg act       768
Ser Val Thr Ala Met Leu Leu His Arg Ala Ile Gly Arg Asn Leu Thr
                    245                 250                 255 tgc gta ttc gtc gac aac ggc ctg ctg cgc ctc aac gaa gca gag cag       816
Cys Val Phe Val Asp Asn Gly Leu Leu Arg Leu Asn Glu Ala Glu Gln
                260                 265                 270 gtt ctg gat atg ttt ggc gat cac ttt ggt ctt aac att gtt cac gta       864
Val Leu Asp Met Phe Gly Asp His Phe Gly Leu Asn Ile Val His Val
            275                 280                 285 ccg gca gaa gat cgc ttc ctg tca gcg ctg gct ggc gaa aac gat ccg       912
Pro Ala Glu Asp Arg Phe Leu Ser Ala Leu Ala Gly Glu Asn Asp Pro
        290                 295                 300 gaa gca aaa cgt aaa atc atc ggt cgc gtt ttc gtt gaa gta ttc gat       960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc      1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca      1056
Ile Tyr Pro Asp Val Ile Glu Ser Ala Ala Ser Ala Thr Gly Lys Ala
            340                 345                 350 cac gtc atc aaa tct cac cac aac gtg ggc ggc ctg ccg aaa gag atg      1104
His Val Ile Lys Ser His His Asn Val Gly Gly Leu Pro Lys Glu Met
        355                 360                 365 aag atg ggc ctg gtt gaa ccg ctg aaa gag ctg ttc aaa gac gaa gtg      1152
Lys Met Gly Leu Val Glu Pro Leu Lys Glu Leu Phe Lys Asp Glu Val
370                 375                 380 cgt aag att ggt ctg gag ctg ggc ctg ccg tac gac atg ctg tac cgt      1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg      1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att      1296
Lys Lys Glu Tyr Cys Asp Leu Leu Arg Arg Ala Asp Ala Ile Phe Ile
            420                 425                 430 gaa gaa ctg cgt aaa gcg gac ctg tac gac aaa gtc agc cag gcg ttc      1344
Glu Glu Leu Arg Lys Ala Asp Leu Tyr Asp Lys Val Ser Gln Ala Phe
        435                 440                 445 act gtg ttc ctg ccg ata cgt tcc gtt ggc gta atg ggc gat ggt cgt      1392
Thr Val Phe Leu Pro Ile Arg Ser Val Gly Val Met Gly Asp Gly Arg
450                 455                 460 aag tat gac tgg gtt gtc tct ctg cgt gct gtc gaa acc atc gac ttt      1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt      1488
Met Thr Ala His Trp Ala His Leu Pro Tyr Asp Phe Leu Gly Arg Val
                485                 490                 495 tcc aac cgc att atc aat gaa gtg aac ggt att tcc cgc gtg gtg tat      1536
Ser Asn Arg Ile Ile Asn Glu Val Asn Gly Ile Ser Arg Val Val Tyr
            500                 505                 510 gac atc agc ggc aag ccg cca gct acc att gag tgg gaa tga              1578
Asp Ile Ser Gly Lys Pro Pro Ala Thr Ile Glu Trp Glu
        515                 520                 525

<210> SEQ ID NO 10
<211> LENGTH: 525
<212> TYPE: PRT
<213> ORGANISM: Artificial Sequence
<220> FEATURE:
```

<223> OTHER INFORMATION: amino acid sequence of G3-1

<400> SEQUENCE: 10

| | | | | | | | | | | | | | | |
|---|---|---|---|---|---|---|---|---|---|---|---|---|---|---|
| Met | Thr | Glu | Asn | Ile | His | Lys | His | Arg | Ile | Leu | Ile | Leu | Asp | Phe | Gly |
| 1 | | | | 5 | | | | | 10 | | | | | 15 | |
| Ser | Gln | Tyr | Thr | Gln | Leu | Val | Ala | Arg | Val | Arg | Glu | Leu | Gly | Val |
| | | | 20 | | | | | 25 | | | | | 30 | |
| Tyr | Cys | Glu | Leu | Trp | Ala | Trp | Asp | Val | Thr | Glu | Ala | Gln | Ile | Arg | Asp |
| | | 35 | | | | | 40 | | | | | 45 | | | |
| Phe | Asn | Pro | Cys | Gly | Ile | Ile | Leu | Ser | Gly | Gly | Pro | Glu | Ser | Thr | Thr |
| | 50 | | | | | 55 | | | | | 60 | | | | |
| Glu | Glu | Asn | Ser | Pro | Arg | Ala | Pro | Gln | Tyr | Val | Phe | Glu | Ala | Gly | Val |
| 65 | | | | | 70 | | | | | 75 | | | | | 80 |
| Pro | Val | Phe | Gly | Val | Cys | Tyr | Gly | Met | Gln | Thr | Met | Ala | Met | Gln | Leu |
| | | | | 85 | | | | | 90 | | | | | 95 | |
| Gly | Gly | His | Val | Glu | Ala | Ser | Asn | Glu | Arg | Glu | Phe | Gly | Tyr | Ala | Gln |
| | | | 100 | | | | | 105 | | | | | 110 | | |
| Val | Glu | Val | Val | Asn | Asp | Ser | Ala | Leu | Val | Arg | Gly | Ile | Glu | Asp | Ala |
| | | 115 | | | | | 120 | | | | | 125 | | | |
| Leu | Thr | Ala | Asp | Gly | Lys | Pro | Leu | Leu | Asp | Val | Trp | Met | Ser | His | Gly |
| | 130 | | | | | 135 | | | | | 140 | | | | |
| Asp | Lys | Val | Thr | Ala | Ile | Pro | Ser | Asp | Phe | Ile | Thr | Val | Ala | Ser | Thr |
| 145 | | | | | 150 | | | | | 155 | | | | | 160 |
| Glu | Ser | Cys | Pro | Phe | Ala | Ile | Met | Ala | Asn | Glu | Glu | Lys | Arg | Phe | Tyr |
| | | | 165 | | | | | 170 | | | | | 175 | | |
| Gly | Val | Gln | Phe | His | Pro | Glu | Val | Thr | His | Thr | Arg | Gln | Gly | Thr | Arg |
| | | | 180 | | | | | 185 | | | | | 190 | | |
| Met | Leu | Glu | Arg | Phe | Val | Arg | Asp | Ile | Cys | Gln | Cys | Glu | Ala | Leu | Trp |
| | | 195 | | | | | 200 | | | | | 205 | | | |
| Thr | Pro | Ala | Lys | Ile | Ile | Asp | Asp | Ala | Val | Ala | Arg | Ile | Arg | Glu | Gln |
| | 210 | | | | | 215 | | | | | 220 | | | | |
| Val | Gly | Asp | Asp | Lys | Val | Ile | Leu | Gly | Leu | Ser | Gly | Gly | Val | Asp | Ser |
| 225 | | | | | 230 | | | | | 235 | | | | | 240 |
| Ser | Val | Thr | Ala | Met | Leu | Leu | His | Arg | Ala | Ile | Gly | Arg | Asn | Leu | Thr |
| | | | | 245 | | | | | 250 | | | | | 255 | |
| Cys | Val | Phe | Val | Asp | Asn | Gly | Leu | Leu | Arg | Leu | Asn | Glu | Ala | Glu | Gln |
| | | | 260 | | | | | 265 | | | | | 270 | | |
| Val | Leu | Asp | Met | Phe | Gly | Asp | His | Phe | Gly | Leu | Asn | Ile | Val | His | Val |
| | | 275 | | | | | 280 | | | | | 285 | | | |
| Pro | Ala | Glu | Asp | Arg | Phe | Leu | Ser | Ala | Leu | Ala | Gly | Glu | Asn | Asp | Pro |
| | 290 | | | | | 295 | | | | | 300 | | | | |
| Glu | Ala | Lys | Arg | Lys | Ile | Ile | Gly | Arg | Val | Phe | Val | Glu | Val | Phe | Asp |
| 305 | | | | | 310 | | | | | 315 | | | | | 320 |
| Glu | Glu | Ala | Leu | Lys | Leu | Glu | Asp | Val | Lys | Trp | Leu | Ala | Gln | Gly | Thr |
| | | | | 325 | | | | | 330 | | | | | 335 | |
| Ile | Tyr | Pro | Asp | Val | Ile | Glu | Ser | Ala | Ala | Ser | Ala | Thr | Gly | Lys | Ala |
| | | | 340 | | | | | 345 | | | | | 350 | | |
| His | Val | Ile | Lys | Ser | His | His | Asn | Val | Gly | Gly | Leu | Pro | Lys | Glu | Met |
| | | 355 | | | | | 360 | | | | | 365 | | | |
| Lys | Met | Gly | Leu | Val | Glu | Pro | Leu | Lys | Glu | Leu | Phe | Lys | Asp | Glu | Val |
| | 370 | | | | | 375 | | | | | 380 | | | | |
| Arg | Lys | Ile | Gly | Leu | Glu | Leu | Gly | Leu | Pro | Tyr | Asp | Met | Leu | Tyr | Arg |
| 385 | | | | | 390 | | | | | 395 | | | | | 400 |
| His | Pro | Phe | Pro | Gly | Pro | Gly | Leu | Gly | Val | Arg | Val | Leu | Gly | Glu | Val |

```
                        405                 410                 415
Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
        435                 440                 445

Thr Val Phe Leu Pro Ile Arg Ser Val Gly Val Met Gly Asp Gly Arg
    450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
            485                 490                 495

Ser Asn Arg Ile Ile Asn Glu Val Asn Gly Ile Ser Arg Val Val Tyr
        500                 505                 510

Asp Ile Ser Gly Lys Pro Pro Ala Thr Ile Glu Trp Glu
    515                 520                 525

<210> SEQ ID NO 11
<211> LENGTH: 1578
<212> TYPE: DNA
<213> ORGANISM: Artificial Sequence
<220> FEATURE:
<223> OTHER INFORMATION: DNA sequence of F12-1
<220> FEATURE:
<221> NAME/KEY: CDS
<222> LOCATION: (1)..(1575)
<223> OTHER INFORMATION: Amino acid sequence of F12-1

<400> SEQUENCE: 11 atg acg gaa aac att cat aag cat cgc atc ctc att ctg gac ttc ggt      48
Met Thr Glu Asn Ile His Lys His Arg Ile Leu Ile Leu Asp Phe Gly
 1               5                  10                  15 tct cag tac act caa ctg gtt gcg cgc cgc gtg cgt gag ctg ggt gtt      96
Ser Gln Tyr Thr Gln Leu Val Ala Arg Arg Val Arg Glu Leu Gly Val
                20                  25                  30 tac tgc gaa ctg tgg gcg tgg gat gtg aca gaa gca caa att cgt gac     144
Tyr Cys Glu Leu Trp Ala Trp Asp Val Thr Glu Ala Gln Ile Arg Asp
            35                  40                  45 ttc aat cca agc ggc att att ctt tcc ggc ggc ccg gaa agt act act     192
Phe Asn Pro Ser Gly Ile Ile Leu Ser Gly Gly Pro Glu Ser Thr Thr
        50                  55                  60 gaa gaa aac agt ccg cgt gcg ccg cag tat gtc ttt gaa gca ggc gta     240
Glu Glu Asn Ser Pro Arg Ala Pro Gln Tyr Val Phe Glu Ala Gly Val
 65                  70                  75                  80 ccg gta ttc ggc gtt tgc tat ggc atg cag acc atg gta atg cag ttg     288
Pro Val Phe Gly Val Cys Tyr Gly Met Gln Thr Met Val Met Gln Leu
                85                  90                  95 ggc ggt cac gtt gaa gcc tct aac gaa cgt gaa ttt ggc tac gcg cag     336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg     384
Val Glu Val Val Asn Asp Ser Ala Leu Val Arg Gly Ile Glu Asp Ala
        115                 120                 125 ctg acc gca gac ggt aaa ccg ctc ctc gat gtc tgg atg agc cac ggc     432
Leu Thr Ala Asp Gly Lys Pro Leu Leu Asp Val Trp Met Ser His Gly
    130                 135                 140 gat aaa gtt acc gct att ccg ccc gac ttc atc acc gta gcc agc acc     480
Asp Lys Val Thr Ala Ile Pro Pro Asp Phe Ile Thr Val Ala Ser Thr
145                 150                 155                 160 gaa agc tgc ccg ttt gcc att atg gct aac gaa gaa aaa cgc ttc tat     528
Glu Ser Cys Pro Phe Ala Ile Met Ala Asn Glu Glu Lys Arg Phe Tyr
                165                 170                 175
```

```
ggc gta cag ttc cac ccg gaa gtg act cat acc cgc cag ggt atg cgc      576
Gly Val Gln Phe His Pro Glu Val Thr His Thr Arg Gln Gly Met Arg
        180                 185                 190 atg ctg gag cgt ttt gtg cgt gat atc tgc cag tgt gaa gcc ctg tgg      624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag      672
Thr Pro Ala Lys Ile Ile Asp Asp Ala Val Ala Arg Ile Arg Glu Gln
    210                 215                 220 gta ggc gac gat aaa gtc atc ctc ggc ctc tct ggt ggt gtg gat tcc      720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act      768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag      816
Cys Val Phe Val Asp Asn Gly Leu Leu Arg Leu Asn Glu Ala Glu Gln
        260                 265                 270 gtt ctg gat atg ttt ggc gat cac ttt ggt ctt aac att gtt cac gta      864
Val Leu Asp Met Phe Gly Asp His Phe Gly Leu Asn Ile Val His Val
    275                 280                 285 ccg gca gaa gat cgc ttc ctg tca gcg ctg gct ggc gaa aac gat ccg      912
Pro Ala Glu Asp Arg Phe Leu Ser Ala Leu Ala Gly Glu Asn Asp Pro
290                 295                 300 gaa gca aaa cgt aaa atc atc ggt cgc gtt ttc gtt gaa gta ttc gat      960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc     1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca     1056
Ile Tyr Pro Asp Val Ile Glu Ser Ala Ala Ser Ala Thr Gly Lys Ala
        340                 345                 350 cac gtc atc aaa tct cac cac aac gtg ggc ggc ctg ccg aaa gag atg     1104
His Val Ile Lys Ser His His Asn Val Gly Gly Leu Pro Lys Glu Met
    355                 360                 365 aag atg ggc ctg gtt gaa ccg ctg aaa gag ctg ttc aaa gac gaa gtg     1152
Lys Met Gly Leu Val Glu Pro Leu Lys Glu Leu Phe Lys Asp Glu Val
370                 375                 380 cgt aag att ggt ctg gag ctg ggc ctg ccg tac gac atg ctg tac cgt     1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg     1248
His Pro Phe Pro Gly Pro Gly Leu Gly Val Arg Val Leu Gly Glu Val
                405                 410                 415 aag aaa gag tac tgt gac ctg ctg cgc cgt gct gat gcc atc ttc att     1296
Lys Lys Glu Tyr Cys Asp Leu Leu Arg Arg Ala Asp Ala Ile Phe Ile
        420                 425                 430 gag gaa ctg cgt aaa gcg gac ctg tac gac aaa gtc agc cag gcg ttc     1344
Glu Glu Leu Arg Lys Ala Asp Leu Tyr Asp Lys Val Ser Gln Ala Phe
    435                 440                 445 act gtg ttc ctg ccg ata cgt tcc gtt ggc gta atg ggc gat ggt cgt     1392
Thr Val Phe Leu Pro Ile Arg Ser Val Gly Val Met Gly Asp Gly Arg
450                 455                 460 aag tat gac tgg gtt gtc tct ctg cgt gct gtc gaa acc atc gac ttt     1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt     1488
Met Thr Ala His Trp Ala His Leu Pro Tyr Asp Phe Leu Gly Arg Val
                485                 490                 495
```

```
tcc aac cgc att atc aat gaa gtg aac ggt att tcc cgc gtg gtg tat    1536
Ser Asn Arg Ile Ile Asn Glu Val Asn Gly Ile Ser Arg Val Val Tyr
            500                 505                 510 gac atc agc ggc aag ccg cca gct acc att gag tgg gaa tga            1578
Asp Ile Ser Gly Lys Pro Pro Ala Thr Ile Glu Trp Glu
            515                 520                 525

<210> SEQ ID NO 12
<211> LENGTH: 525
<212> TYPE: PRT
<213> ORGANISM: Artificial Sequence
<220> FEATURE:
<223> OTHER INFORMATION: amino acid sequence of F12-1

<400> SEQUENCE: 12

Met Thr Glu Asn Ile His Lys His Arg Ile Leu Ile Leu Asp Phe Gly
 1               5                  10                  15

Ser Gln Tyr Thr Gln Leu Val Ala Arg Val Arg Glu Leu Gly Val
            20                  25                  30

Tyr Cys Glu Leu Trp Ala Trp Asp Val Thr Glu Ala Gln Ile Arg Asp
        35                  40                  45

Phe Asn Pro Ser Gly Ile Ile Leu Ser Gly Gly Pro Glu Ser Thr Thr
    50                  55                  60

Glu Glu Asn Ser Pro Arg Ala Pro Gln Tyr Val Phe Glu Ala Gly Val
65                  70                  75                  80

Pro Val Phe Gly Val Cys Tyr Gly Met Gln Thr Met Val Met Gln Leu
                85                  90                  95

Gly Gly His Val Glu Ala Ser Asn Glu Arg Glu Phe Gly Tyr Ala Gln
            100                 105                 110

Val Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
    130                 135                 140

Asp Lys Val Thr Ala Ile Pro Pro Asp Phe Ile Thr Val Ala Ser Thr
145                 150                 155                 160

Glu Ser Cys Pro Phe Ala Ile Met Ala Asn Glu Lys Arg Phe Tyr
                165                 170                 175

Gly Val Gln Phe His Pro Glu Val Thr His Thr Arg Gln Gly Met Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
    210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
    290                 295                 300

Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
```

```
                        325                 330                 335
Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
        355                 360                 365

Lys Met Gly Leu Val Glu Pro Leu Lys Glu Leu Phe Lys Asp Glu Val
    370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
        435                 440                 445

Thr Val Phe Leu Pro Ile Arg Ser Val Gly Val Met Gly Asp Gly Arg
    450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
        515                 520                 525

<210> SEQ ID NO 13
<211> LENGTH: 1578
<212> TYPE: DNA
<213> ORGANISM: Artificial Sequence
<220> FEATURE:
<223> OTHER INFORMATION: DNA sequence of F63-1
<220> FEATURE:
<221> NAME/KEY: CDS
<222> LOCATION: (1)..(1575)
<223> OTHER INFORMATION: Amino acid sequence of F63-1

<400> SEQUENCE: 13 atg acg gaa aac att cat aag cat cgc atc ctc att ctg gac ttc ggt        48
Met Thr Glu Asn Ile His Lys His Arg Ile Leu Ile Leu Asp Phe Gly
 1               5                  10                  15 tct cag tac act caa ctg gtt gcg cgc cgc gtg cgt gag ctg ggt gtt        96
Ser Gln Tyr Thr Gln Leu Val Ala Arg Arg Val Arg Glu Leu Gly Val
                20                  25                  30 tac tgc gaa ctg tgg gcg tgg gat gtg aca gaa gca caa att cgt gac       144
Tyr Cys Glu Leu Trp Ala Trp Asp Val Thr Glu Ala Gln Ile Arg Asp
            35                  40                  45 ttc aat cca agc ggc att att ctt tcc ggc ggc ccg gaa agt act act       192
Phe Asn Pro Ser Gly Ile Ile Leu Ser Gly Gly Pro Glu Ser Thr Thr
        50                  55                  60 gaa gaa aac agt ccg cgt gcg ccg cag tat gtc ttt gaa gca ggc gta       240
Glu Glu Asn Ser Pro Arg Ala Pro Gln Tyr Val Phe Glu Ala Gly Val
 65                  70                  75                  80 ccg gta ttc ggc gtt tgc tat ggc atg cag acc atg gta atg cag ttg       288
Pro Val Phe Gly Val Cys Tyr Gly Met Gln Thr Met Val Met Gln Leu
                85                  90                  95 ggc ggt cac att gaa gcc tct aac gaa cgt gaa ttt ggc tac gcg cag       336
Gly Gly His Ile Glu Ala Ser Asn Glu Arg Glu Phe Gly Tyr Ala Gln
               100                 105                 110
```

```
gct gaa gtc gta aac gac agc gca ctg gtt cgc ggt atc gaa gat gcg    384
Ala Glu Val Val Asn Asp Ser Ala Leu Val Arg Gly Ile Glu Asp Ala
    115                 120                 125 ctg acc gca gac ggt aaa ccg ctg ctc gat gtc tgg atg agc cac ggc    432
Leu Thr Ala Asp Gly Lys Pro Leu Leu Asp Val Trp Met Ser His Gly
130                 135                 140 gat aaa gtt acc gct att ccg tcc gac ttc atc acc gta gcc agc acc    480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat    528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt acg cgc    576
Gly Val Gln Phe His Pro Glu Val Thr His Thr Arg Gln Gly Thr Arg
            180                 185                 190 atg ctg gag cgt ttt gtg cgt gat atc tgc cag tgt gaa gcc ctg tgg    624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag    672
Thr Pro Ala Lys Ile Ile Asp Asp Ala Val Ala Arg Ile Arg Glu Gln
    210                 215                 220 gta ggc gac gat aaa gtt atc ctc ggc ctc tct ggt ggt gtg gat tcc    720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act    768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag    816
Cys Val Phe Val Asp Asn Gly Leu Leu Arg Leu Asn Glu Ala Glu Gln
            260                 265                 270 gtt ctg gat atg ttt ggc gat cac ttt ggt ctt aac att gtt cac gta    864
Val Leu Asp Met Phe Gly Asp His Phe Gly Leu Asn Ile Val His Val
        275                 280                 285 ccg gca gaa gat cgc ttc ctg tca gcg ctg gct ggc gaa aac gat ccg    912
Pro Ala Glu Asp Arg Phe Leu Ser Ala Leu Ala Gly Glu Asn Asp Pro
    290                 295                 300 gaa gca aaa cgt aaa atc atc ggt cgc gtt ttc gtt gaa gta ttc gat    960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc    1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca    1056
Ile Tyr Pro Asp Val Ile Glu Ser Ala Ala Ser Ala Thr Gly Lys Ala
            340                 345                 350 cac gtc atc aaa tct cac cac aac gtg ggc ggc ctg ccg aaa gag atg    1104
His Val Ile Lys Ser His His Asn Val Gly Gly Leu Pro Lys Glu Met
        355                 360                 365 aag atg ggc ctg gtt gaa ccg ctg aaa gag ctg ttc aaa gac gaa gtg    1152
Lys Met Gly Leu Val Glu Pro Leu Lys Glu Leu Phe Lys Asp Glu Val
    370                 375                 380 cgt aag att ggt ctg gag ctg ggc ctg ccg tac gac atg ctg tac cgt    1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg    1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att    1296
Lys Lys Glu Tyr Cys Asp Leu Leu Arg Arg Ala Asp Ala Ile Phe Ile
            420                 425                 430
```

```
gaa gaa ctg cgt aaa gcg gac ctg tac gac aaa gtc agc cag gcg ttc      1344
Glu Glu Leu Arg Lys Ala Asp Leu Tyr Asp Lys Val Ser Gln Ala Phe
        435                 440                 445 act gtg ttc ctg ccg ata cgt tcc gtt ggc gta atg ggc gat ggt cgt      1392
Thr Val Phe Leu Pro Ile Arg Ser Val Gly Val Met Gly Asp Gly Arg
    450                 455                 460 aag tat ggc tgg gtt gtc tct ctg cgt gct gtc gaa acc atc gac ttt      1440
Lys Tyr Gly Trp Val Val Ser Leu Arg Ala Val Glu Thr Ile Asp Phe
465                 470                 475                 480 atg acc gca cac tgg gcg cat ctg ccg tac gat ttc ctc ggt cgc gtt      1488
Met Thr Ala His Trp Ala His Leu Pro Tyr Asp Phe Leu Gly Arg Val
                485                 490                 495 tcc aac cgc att atc aat gaa gtg aac ggt att tcc cgc gtg gtg tat      1536
Ser Asn Arg Ile Ile Asn Glu Val Asn Gly Ile Ser Arg Val Val Tyr
            500                 505                 510 gac atc agc ggc aag ccg cca gct acc att gag tgg gaa tga              1578
Asp Ile Ser Gly Lys Pro Pro Ala Thr Ile Glu Trp Glu
        515                 520                 525

<210> SEQ ID NO 14
<211> LENGTH: 525
<212> TYPE: PRT
<213> ORGANISM: Artificial Sequence
<220> FEATURE:
<223> OTHER INFORMATION: amino acid sequence of F63-1

<400> SEQUENCE: 14

Met Thr Glu Asn Ile His Lys His Arg Ile Leu Ile Leu Asp Phe Gly
  1               5                  10                  15

Ser Gln Tyr Thr Gln Leu Val Ala Arg Arg Val Arg Glu Leu Gly Val
                 20                  25                  30

Tyr Cys Glu Leu Trp Ala Trp Asp Val Thr Glu Ala Gln Ile Arg Asp
             35                  40                  45

Phe Asn Pro Ser Gly Ile Ile Leu Ser Gly Gly Pro Glu Ser Thr Thr
         50                  55                  60

Glu Glu Asn Ser Pro Arg Ala Pro Gln Tyr Val Phe Glu Ala Gly Val
 65                  70                  75                  80

Pro Val Phe Gly Val Cys Tyr Gly Met Gln Thr Met Val Met Gln Leu
                 85                  90                  95

Gly Gly His Ile Glu Ala Ser Asn Glu Arg Glu Phe Gly Tyr Ala Gln
            100                 105                 110

Ala Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
    130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Glu Lys Arg Phe Tyr
                165                 170                 175

Gly Val Gln Phe His Pro Glu Val Thr His Thr Arg Gln Gly Thr Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
    210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
```

```
                    245                 250                 255
Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
    290                 295                 300

Glu Ala Lys Arg Lys Ile Ile Gly Arg Val Phe Glu Val Phe Asp
305                 310                 315                 320

Glu Glu Ala Leu Lys Leu Glu Asp Val Lys Trp Leu Ala Gln Gly Thr
                325                 330                 335

Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
        355                 360                 365

Lys Met Gly Leu Val Glu Pro Leu Lys Glu Leu Phe Lys Asp Glu Val
    370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
        435                 440                 445

Thr Val Phe Leu Pro Ile Arg Ser Val Gly Val Met Gly Asp Gly Arg
    450                 455                 460

Lys Tyr Gly Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
        515                 520                 525

<210> SEQ ID NO 15
<211> LENGTH: 1578
<212> TYPE: DNA
<213> ORGANISM: Artificial Sequence
<220> FEATURE:
<223> OTHER INFORMATION: DNA sequence of G1C
<220> FEATURE:
<221> NAME/KEY: CDS
<222> LOCATION: (1)..(1575)
<223> OTHER INFORMATION: Amino acid sequence of G1C

<400> SEQUENCE: 15 atg acg gaa aac att cat aag cat cgc atc ctc att ctg gac ttc ggt     48
Met Thr Glu Asn Ile His Lys His Arg Ile Leu Ile Leu Asp Phe Gly
  1               5                  10                  15 tct cag tac act caa ctg gtt gcg cgc cgc gtg cgt gag ctg ggt gtt     96
Ser Gln Tyr Thr Gln Leu Val Ala Arg Arg Val Arg Glu Leu Gly Val
             20                  25                  30 tac tgc gaa ctg tgg gcg tgg gat gtg aca gaa gca caa att cgt gac    144
Tyr Cys Glu Leu Trp Ala Trp Asp Val Thr Glu Ala Gln Ile Arg Asp
         35                  40                  45 ttc aat cca agc ggc att att ctt tcc ggc ggc ccg gaa agt act act    192
```

```
Phe Asn Pro Ser Gly Ile Ile Leu Ser Gly Gly Pro Glu Ser Thr Thr
 50                  55                  60 gaa gaa aac agt ccg cgt gcg ccg cag tat gtc ttt gaa gca ggc gta        240
Glu Glu Asn Ser Pro Arg Ala Pro Gln Tyr Val Phe Glu Ala Gly Val
 65                  70                  75                  80 ccg gta ttc ggc gtt gca tat ggc atg cag acc atg gca atg cag ttg        288
Pro Val Phe Gly Val Ala Tyr Gly Met Gln Thr Met Ala Met Gln Leu
                     85                  90                  95 ggc ggt cac gtt gaa gcc tct aac gaa cgt gaa ttt ggc tac gcg cag        336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg        384
Val Glu Val Val Asn Asp Ser Ala Leu Val Arg Gly Ile Glu Asp Ala
        115                 120                 125 ctg acc gca gac ggt aaa ccg ctg ctc gat gtc tgg atg agc cac ggc        432
Leu Thr Ala Asp Gly Lys Pro Leu Leu Asp Val Trp Met Ser His Gly
130                 135                 140 gat aaa gtt acc gct att ccg tcc gac ttc atc acc gta gcc agc acc        480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat        528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt atg cgc        576
Gly Val Gln Phe His Pro Glu Val Thr His Thr Arg Gln Gly Met Arg
            180                 185                 190 atg ctg gag cgt ttt gtg cgt gat atc tgc cag tgt gaa gcc ctg tgg        624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag        672
Thr Pro Ala Lys Ile Ile Asp Asp Ala Val Ala Arg Ile Arg Glu Gln
210                 215                 220 gta ggc gac gat aaa gtc atc ctc ggc ctc tct ggt ggt gtg gat tcc        720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act        768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag        816
Cys Val Phe Val Asp Asn Gly Leu Leu Arg Leu Asn Glu Ala Glu Gln
            260                 265                 270 gtt ctg gat atg ttt ggc gat cac ttt ggt ctt aac att gtt cac gta        864
Val Leu Asp Met Phe Gly Asp His Phe Gly Leu Asn Ile Val His Val
        275                 280                 285 ccg gca gaa gat cgc ttc ctg tca gcg ctg gct ggc gaa aac gat ccg        912
Pro Ala Glu Asp Arg Phe Leu Ser Ala Leu Ala Gly Glu Asn Asp Pro
290                 295                 300 gaa gca aaa cgt aaa atc atc ggt cgc gtt ttc gtt gaa gta ttc gat        960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc       1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca       1056
Ile Tyr Pro Asp Val Ile Glu Ser Ala Ala Ser Ala Thr Gly Lys Ala
            340                 345                 350 cac gtc atc aaa tct cac cac aac gtg ggc ggc ctg ccg aaa gag atg       1104
His Val Ile Lys Ser His His Asn Val Gly Gly Leu Pro Lys Glu Met
        355                 360                 365 aag atg ggc ctg gtt gaa ccg ctg aaa gag ctg ttc aaa gac gaa gtg       1152
```

```
cgt aag att ggt ctg gag ctg ggc ctg ccg tac gac atg ctg tac cgt    1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg    1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att    1296
Lys Lys Glu Tyr Cys Asp Leu Leu Arg Arg Ala Asp Ala Ile Phe Ile
            420                 425                 430 gaa gaa ctg cgt aaa gcg gac ctg tac gac aaa gtc agc cag gcg ttc    1344
Glu Glu Leu Arg Lys Ala Asp Leu Tyr Asp Lys Val Ser Gln Ala Phe
        435                 440                 445 act gtg ttc ctg ccg gta cgt tcc gtt ggc gta atg ggc gat ggt cgt    1392
Thr Val Phe Leu Pro Val Arg Ser Val Gly Val Met Gly Asp Gly Arg
    450                 455                 460 aag tat gac tgg gtt gtc tct ctg cgt gct gtc gaa acc atc gac ttt    1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt    1488
Met Thr Ala His Trp Ala His Leu Pro Tyr Asp Phe Leu Gly Arg Val
                485                 490                 495 tcc aac cgc att atc aat gaa gtg aac ggt att tcc cgc gtg gtg tat    1536
Ser Asn Arg Ile Ile Asn Glu Val Asn Gly Ile Ser Arg Val Val Tyr
            500                 505                 510 gac atc agc ggc aag ccg cca gct acc att gag tgg gaa tga             1578
Asp Ile Ser Gly Lys Pro Pro Ala Thr Ile Glu Trp Glu
        515                 520                 525

<210> SEQ ID NO 16
<211> LENGTH: 525
<212> TYPE: PRT
<213> ORGANISM: Artificial Sequence
<220> FEATURE:
<223> OTHER INFORMATION: amino acid sequence of G1C

<400> SEQUENCE: 16

Met Thr Glu Asn Ile His Lys His Arg Ile Leu Ile Leu Asp Phe Gly
1               5                   10                  15

Ser Gln Tyr Thr Gln Leu Val Ala Arg Arg Val Arg Glu Leu Gly Val
            20                  25                  30

Tyr Cys Glu Leu Trp Ala Trp Asp Val Thr Glu Ala Gln Ile Arg Asp
        35                  40                  45

Phe Asn Pro Ser Gly Ile Ile Leu Ser Gly Gly Pro Glu Ser Thr Thr
    50                  55                  60

Glu Glu Asn Ser Pro Arg Ala Pro Gln Tyr Val Phe Glu Ala Gly Val
65                  70                  75                  80

Pro Val Phe Gly Val Ala Tyr Gly Met Gln Thr Met Ala Met Gln Leu
                85                  90                  95

Gly Gly His Val Glu Ala Ser Asn Glu Arg Glu Phe Gly Tyr Ala Gln
            100                 105                 110

Val Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
    130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Glu Lys Arg Phe Tyr
```

```
                        165                 170                 175
Gly Val Gln Phe His Pro Glu Val Thr His Thr Arg Gln Gly Met Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
    210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
    290                 295                 300

Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
                325                 330                 335

Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
        355                 360                 365

Lys Met Gly Leu Val Glu Pro Leu Lys Glu Leu Phe Lys Asp Glu Val
    370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
        435                 440                 445

Thr Val Phe Leu Pro Val Arg Ser Val Gly Val Met Gly Asp Gly Arg
    450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
        515                 520                 525

<210> SEQ ID NO 17
<211> LENGTH: 1578
<212> TYPE: DNA
<213> ORGANISM: Artificial Sequence
<220> FEATURE:
<223> OTHER INFORMATION: DNA sequence of G3C
<220> FEATURE:
<221> NAME/KEY: CDS
<222> LOCATION: (1)..(1575)
<223> OTHER INFORMATION: Amino acid sequence of G3C
```

<400> SEQUENCE: 17

```
atg acg gaa aac att cat aag cat cgc atc ctc att ctg gac ttc ggt       48
Met Thr Glu Asn Ile His Lys His Arg Ile Leu Ile Leu Asp Phe Gly
 1               5                  10                  15 tct cag tac act caa ctg gtt gcg cgc gtg cgt gag ctg ggt gtt           96
Ser Gln Tyr Thr Gln Leu Val Ala Arg Val Arg Glu Leu Gly Val
             20                  25                  30 tac tgc gaa ttg tgg gcg tgg gat gtg aca gaa gca caa att cgt gac      144
Tyr Cys Glu Leu Trp Ala Trp Asp Val Thr Glu Ala Gln Ile Arg Asp
         35                  40                  45 ttc aat cca tgc ggc att att ctt tcc ggc ggc ccg gaa agt act act      192
Phe Asn Pro Cys Gly Ile Ile Leu Ser Gly Gly Pro Glu Ser Thr Thr
 50                  55                  60 gaa gaa aac agt ccg cgt gcg ccg cag tat gtc ttt gaa gca ggc gta      240
Glu Glu Asn Ser Pro Arg Ala Pro Gln Tyr Val Phe Glu Ala Gly Val
 65                  70                  75                  80 ccg gta ttc ggc gtt gca tat ggc atg cag acc atg gca atg cag ttg      288
Pro Val Phe Gly Val Ala Tyr Gly Met Gln Thr Met Ala Met Gln Leu
             85                  90                  95 ggc ggt cac gtt gaa gcc tct aac gaa cgt gaa ttt ggc tac gcg cag      336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg      384
Val Glu Val Val Asn Asp Ser Ala Leu Val Arg Gly Ile Glu Asp Ala
            115                 120                 125 ctg acc gca gac ggt aaa ccg ctg ctc gat gtc tgg atg agc cac ggc      432
Leu Thr Ala Asp Gly Lys Pro Leu Leu Asp Val Trp Met Ser His Gly
130                 135                 140 gat aaa gtt acc gct att ccg tcc gac ttc atc acc gta gcc agc acc      480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat      528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt acg cgc      576
Gly Val Gln Phe His Pro Glu Val Thr His Thr Arg Gln Gly Thr Arg
            180                 185                 190 atg ctg gag cgt ttt gtg cgt gat atc tgc cag tgt gaa gcc ctg tgg      624
Met Leu Glu Arg Phe Val Arg Asp Ile Cys Gln Cys Glu Ala Leu Trp
            195                 200                 205 acg cca gcg aaa att atc gac gat gct gta gct cgc atc cgc gag cag      672
Thr Pro Ala Lys Ile Ile Asp Asp Ala Val Ala Arg Ile Arg Glu Gln
        210                 215                 220 gta ggc gac gat aaa gtc atc ctc ggc ctc tct ggt ggt gtg gat tcc      720
Val Gly Asp Asp Lys Val Ile Leu Gly Leu Ser Gly Gly Val Asp Ser
225                 230                 235                 240 tcc gta acc gca atg ctg ctg cac cgc gct atc ggt aga aac ctg act      768
Ser Val Thr Ala Met Leu Leu His Arg Ala Ile Gly Arg Asn Leu Thr
                245                 250                 255 tgc gta ttc gtc gac aac ggc ctg ctg cgc ctc aac gaa gca gag cag      816
Cys Val Phe Val Asp Asn Gly Leu Leu Arg Leu Asn Glu Ala Glu Gln
            260                 265                 270 gtt ctg gat atg ttt ggc gat cac ttt ggt ctt aac att gtt cac gta      864
Val Leu Asp Met Phe Gly Asp His Phe Gly Leu Asn Ile Val His Val
            275                 280                 285 ccg gca gaa gat cgc ttc ctg tca gcg ctg gct ggc gaa aac gat ccg      912
Pro Ala Glu Asp Arg Phe Leu Ser Ala Leu Ala Gly Glu Asn Asp Pro
        290                 295                 300 gaa gca aaa cgt aaa atc atc ggt cgc gtt ttc gtt gaa gta ttc gat      960
Glu Ala Lys Arg Lys Ile Ile Gly Arg Val Phe Val Glu Val Phe Asp
```

```
                    305                 310                 315                 320
gaa gaa gcg ctg aaa ctg gaa gac gtg aag tgg ctg gcg cag ggc acc            1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca            1056
Ile Tyr Pro Asp Val Ile Glu Ser Ala Ala Ser Ala Thr Gly Lys Ala
            340                 345                 350 cac gtc atc aaa tct cac cac aac gtg ggc ggc ctg ccg aaa gag atg            1104
His Val Ile Lys Ser His His Asn Val Gly Gly Leu Pro Lys Glu Met
        355                 360                 365 aag atg ggc ctg gtt gaa ccg ctg aaa gag ctg ttc aaa gac gaa gtg            1152
Lys Met Gly Leu Val Glu Pro Leu Lys Glu Leu Phe Lys Asp Glu Val
    370                 375                 380 cgt aag att ggt ctg gag ctg ggc ctg ccg tac gac atg ctg tac cgt            1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg            1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att            1296
Lys Lys Glu Tyr Cys Asp Leu Leu Arg Arg Ala Asp Ala Ile Phe Ile
            420                 425                 430 gaa gaa ctg cgt aaa gcg gac ctg tac gac aaa gtc agc cag gcg ttc            1344
Glu Glu Leu Arg Lys Ala Asp Leu Tyr Asp Lys Val Ser Gln Ala Phe
        435                 440                 445 act gtg ttc ctg ccg ata cgt tcc gtt ggc gta atg ggc gat ggt cgt            1392
Thr Val Phe Leu Pro Ile Arg Ser Val Gly Val Met Gly Asp Gly Arg
    450                 455                 460 aag tat gac tgg gtt gtc tct ctg cgt gct gtc gaa acc atc gac ttt            1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt            1488
Met Thr Ala His Trp Ala His Leu Pro Tyr Asp Phe Leu Gly Arg Val
                485                 490                 495 tcc aac cgc att atc aat gaa gtg aac ggt att tcc cgc gtg gtg tat            1536
Ser Asn Arg Ile Ile Asn Glu Val Asn Gly Ile Ser Arg Val Val Tyr
            500                 505                 510 gac atc agc ggc aag ccg cca gct acc att gag tgg gaa tga                    1578
Asp Ile Ser Gly Lys Pro Pro Ala Thr Ile Glu Trp Glu
        515                 520                 525

<210> SEQ ID NO 18
<211> LENGTH: 525
<212> TYPE: PRT
<213> ORGANISM: Artificial Sequence
<220> FEATURE:
<223> OTHER INFORMATION: amino acid sequence of G3C

<400> SEQUENCE: 18

Met Thr Glu Asn Ile His Lys His Arg Ile Leu Ile Leu Asp Phe Gly
1               5                   10                  15

Ser Gln Tyr Thr Gln Leu Val Ala Arg Arg Val Arg Glu Leu Gly Val
            20                  25                  30

Tyr Cys Glu Leu Trp Ala Trp Asp Val Thr Glu Ala Gln Ile Arg Asp
        35                  40                  45

Phe Asn Pro Cys Gly Ile Ile Leu Ser Gly Gly Pro Glu Ser Thr Thr
    50                  55                  60

Glu Glu Asn Ser Pro Arg Ala Pro Gln Tyr Val Phe Glu Ala Gly Val
65                  70                  75                  80

Pro Val Phe Gly Val Ala Tyr Gly Met Gln Thr Met Ala Met Gln Leu
```

-continued

```
                    85                  90                  95
Gly Gly His Val Glu Ala Ser Asn Arg Glu Phe Gly Tyr Ala Gln
                100                 105                 110
Val Glu Val Asn Asp Ser Ala Leu Val Arg Gly Ile Glu Asp Ala
                115                 120                 125
Leu Thr Ala Asp Gly Lys Pro Leu Leu Asp Val Trp Met Ser His Gly
                130                 135                 140
Asp Lys Val Thr Ala Ile Pro Ser Asp Phe Ile Thr Val Ala Ser Thr
145                 150                 155                 160
Glu Ser Cys Pro Phe Ala Ile Met Ala Asn Glu Glu Lys Arg Phe Tyr
                165                 170                 175
Gly Val Gln Phe His Pro Glu Val Thr His Thr Arg Gln Gly Thr Arg
                180                 185                 190
Met Leu Glu Arg Phe Val Arg Asp Ile Cys Gln Cys Glu Ala Leu Trp
                195                 200                 205
Thr Pro Ala Lys Ile Ile Asp Asp Ala Val Ala Arg Ile Arg Glu Gln
                210                 215                 220
Val Gly Asp Asp Lys Val Ile Leu Gly Leu Ser Gly Gly Val Asp Ser
225                 230                 235                 240
Ser Val Thr Ala Met Leu Leu His Arg Ala Ile Gly Arg Asn Leu Thr
                245                 250                 255
Cys Val Phe Val Asp Asn Gly Leu Leu Arg Leu Asn Glu Ala Glu Gln
                260                 265                 270
Val Leu Asp Met Phe Gly Asp His Phe Gly Leu Asn Ile Val His Val
                275                 280                 285
Pro Ala Glu Asp Arg Phe Leu Ser Ala Leu Ala Gly Glu Asn Asp Pro
                290                 295                 300
Glu Ala Lys Arg Lys Ile Ile Gly Arg Val Phe Val Glu Val Phe Asp
305                 310                 315                 320
Glu Glu Ala Leu Lys Leu Glu Asp Val Lys Trp Leu Ala Gln Gly Thr
                325                 330                 335
Ile Tyr Pro Asp Val Ile Glu Ser Ala Ala Ser Ala Thr Gly Lys Ala
                340                 345                 350
His Val Ile Lys Ser His His Asn Val Gly Gly Leu Pro Lys Glu Met
                355                 360                 365
Lys Met Gly Leu Val Glu Pro Leu Lys Glu Leu Phe Lys Asp Glu Val
                370                 375                 380
Arg Lys Ile Gly Leu Glu Leu Gly Leu Pro Tyr Asp Met Leu Tyr Arg
385                 390                 395                 400
His Pro Phe Pro Gly Pro Gly Leu Gly Val Arg Val Leu Gly Glu Val
                405                 410                 415
Lys Lys Glu Tyr Cys Asp Leu Leu Arg Arg Ala Asp Ala Ile Phe Ile
                420                 425                 430
Glu Glu Leu Arg Lys Ala Asp Leu Tyr Asp Lys Val Ser Gln Ala Phe
                435                 440                 445
Thr Val Phe Leu Pro Ile Arg Ser Val Gly Val Met Gly Asp Gly Arg
                450                 455                 460
Lys Tyr Asp Trp Val Val Ser Leu Arg Ala Val Glu Thr Ile Asp Phe
465                 470                 475                 480
Met Thr Ala His Trp Ala His Leu Pro Tyr Asp Phe Leu Gly Arg Val
                485                 490                 495
Ser Asn Arg Ile Ile Asn Glu Val Asn Gly Ile Ser Arg Val Val Tyr
                500                 505                 510
```

```
Asp Ile Ser Gly Lys Pro Pro Ala Thr Ile Glu Trp Glu
        515                 520                 525

<210> SEQ ID NO 19
<211> LENGTH: 1578
<212> TYPE: DNA
<213> ORGANISM: Artificial Sequence
<220> FEATURE:
<223> OTHER INFORMATION: DNA sequence of F12C
<220> FEATURE:
<221> NAME/KEY: CDS
<222> LOCATION: (1)...(1575)
<223> OTHER INFORMATION: amino acids sequence of F12C

<400> SEQUENCE: 19 atg acg gaa aac att cat aag cat cgc atc ctc att ctg gac ttc ggt      48
Met Thr Glu Asn Ile His Lys His Arg Ile Leu Ile Leu Asp Phe Gly
  1               5                  10                  15 tct cag tac act caa ctg gtt gcg cgc cgc gtg cgt gag ctg ggt gtt      96
Ser Gln Tyr Thr Gln Leu Val Ala Arg Arg Val Arg Glu Leu Gly Val
             20                  25                  30 tac tgc gaa ctg tgg gcg tgg gat gtg aca gaa gca caa att cgt gac     144
Tyr Cys Glu Leu Trp Ala Trp Asp Val Thr Glu Ala Gln Ile Arg Asp
         35                  40                  45 ttc aat cca agc ggc att att ctt tcc ggc ggc ccg gaa agt act act     192
Phe Asn Pro Ser Gly Ile Ile Leu Ser Gly Gly Pro Glu Ser Thr Thr
     50                  55                  60 gaa gaa aac agt ccg cgt gcg ccg cag tat gtc ttt gaa gca ggc gta     240
Glu Glu Asn Ser Pro Arg Ala Pro Gln Tyr Val Phe Glu Ala Gly Val
 65                  70                  75                  80 ccg gta ttc ggc gtt gca tat ggc atg cag acc atg gta atg cag ttg     288
Pro Val Phe Gly Val Ala Tyr Gly Met Gln Thr Met Val Met Gln Leu
                 85                  90                  95 ggc ggt cac gtt gaa gcc tct aac gaa cgt gaa ttt ggc tac gcg cag     336
Gly Gly His Val Glu Ala Ser Asn Glu Arg Glu Phe Gly Tyr Ala Gln
            100                 105                 110 gtt gaa gtc gta aac gac agc gca ctg gtt cgc ggt atc gaa gat gcg     384
Val Glu Val Val Asn Asp Ser Ala Leu Val Arg Gly Ile Glu Asp Ala
        115                 120                 125 ctg acc gca gac ggt aaa ccg ctg ctc gat gtc tgg atg agc cac ggc     432
Leu Thr Ala Asp Gly Lys Pro Leu Leu Asp Val Trp Met Ser His Gly
    130                 135                 140 gat aaa gtt acc gct att ccg ccc gac ttc atc acc gta gcc agc acc     480
Asp Lys Val Thr Ala Ile Pro Pro Asp Phe Ile Thr Val Ala Ser Thr
145                 150                 155                 160 gaa agc tgc ccg ttt gcc att atg gct aac gaa gaa aaa cgc ttc tat     528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt atg cgc     576
Gly Val Gln Phe His Pro Glu Val Thr His Thr Arg Gln Gly Met Arg
            180                 185                 190 atg ctg gag cgt ttt gtg cgt gat atc tgc cag tgt gaa gcc ctg tgg     624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag     672
Thr Pro Ala Lys Ile Ile Asp Asp Ala Val Ala Arg Ile Arg Glu Gln
    210                 215                 220 gta ggc gac gat aaa gtc atc ctc ggc ctc tct ggt ggt gtg gat tcc     720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act     768
Ser Val Thr Ala Met Leu Leu His Arg Ala Ile Gly Lys Asn Leu Thr
                245                 250                 255
```

| | | | | | | | | | | | | | | | | |
|---|---|---|---|---|---|---|---|---|---|---|---|---|---|---|---|---|
| tgc | gta | ttc | gtc | gac | aac | ggc | ctg | ctg | cgc | ctc | aac | gaa | gca | gag | cag | 816 |
| Cys | Val | Phe | Val | Asp | Asn | Gly | Leu | Leu | Arg | Leu | Asn | Glu | Ala | Glu | Gln | |
| | | | 260 | | | | 265 | | | | 270 | | | | | |
| gtt | ctg | gat | atg | ttt | ggc | gat | cac | ttt | ggt | ctt | aac | att | gtt | cac | gta | 864 |
| Val | Leu | Asp | Met | Phe | Gly | Asp | His | Phe | Gly | Leu | Asn | Ile | Val | His | Val | |
| | | | 275 | | | | 280 | | | | 285 | | | | | |
| ccg | gca | gaa | gat | cgc | ttc | ctg | tca | gcg | ctg | gct | ggc | gaa | aac | gat | ccg | 912 |
| Pro | Ala | Glu | Asp | Arg | Phe | Leu | Ser | Ala | Leu | Ala | Gly | Glu | Asn | Asp | Pro | |
| | | 290 | | | | | 295 | | | | 300 | | | | | |
| gaa | gca | aaa | cgt | aaa | atc | atc | ggt | cgc | gtt | ttc | gtt | gaa | gta | ttc | gat | 960 |
| Glu | Ala | Lys | Arg | Lys | Ile | Ile | Gly | Arg | Val | Phe | Val | Glu | Val | Phe | Asp | |
| 305 | | | | | 310 | | | | | 315 | | | | | 320 | |
| gaa | gaa | gcg | ctg | aaa | ctg | gaa | gac | gtg | aag | tgg | ctg | gcg | cag | ggc | acc | 1008 |
| Glu | Glu | Ala | Leu | Lys | Leu | Glu | Asp | Val | Lys | Trp | Leu | Ala | Gln | Gly | Thr | |
| | | | | 325 | | | | | 330 | | | | | 335 | | |
| atc | tac | cct | gac | gtt | atc | gaa | tct | gcg | gcg | tct | gca | acc | ggt | aaa | gca | 1056 |
| Ile | Tyr | Pro | Asp | Val | Ile | Glu | Ser | Ala | Ala | Ser | Ala | Thr | Gly | Lys | Ala | |
| | | | 340 | | | | 345 | | | | 350 | | | | | |
| cac | gtc | atc | aaa | tct | cac | cac | aac | gtg | ggc | ggc | ctg | ccg | aaa | gag | atg | 1104 |
| His | Val | Ile | Lys | Ser | His | His | Asn | Val | Gly | Gly | Leu | Pro | Lys | Glu | Met | |
| | | | 355 | | | | 360 | | | | 365 | | | | | |
| aag | atg | ggc | ctg | gtt | gaa | ccg | ctg | aaa | gag | ctg | ttc | aaa | gac | gaa | gtg | 1152 |
| Lys | Met | Gly | Leu | Val | Glu | Pro | Leu | Lys | Glu | Leu | Phe | Lys | Asp | Glu | Val | |
| | 370 | | | | | 375 | | | | | 380 | | | | | |
| cgt | aag | att | ggt | ctg | gag | ctg | ggc | ctg | ccg | tac | gac | atg | ctg | tac | cgt | 1200 |
| Arg | Lys | Ile | Gly | Leu | Glu | Leu | Gly | Leu | Pro | Tyr | Asp | Met | Leu | Tyr | Arg | |
| 385 | | | | | 390 | | | | | 395 | | | | | 400 | |
| cac | ccg | ttc | ccg | gga | cca | ggc | ctt | ggc | gtt | cgt | gtt | ctg | ggt | gaa | gtg | 1248 |
| His | Pro | Phe | Pro | Gly | Pro | Gly | Leu | Gly | Val | Arg | Val | Leu | Gly | Glu | Val | |
| | | | | 405 | | | | | 410 | | | | | 415 | | |
| aag | aaa | gag | tac | tgt | gac | ctg | ctg | cgc | cgt | gct | gat | gcc | atc | ttc | att | 1296 |
| Lys | Lys | Glu | Tyr | Cys | Asp | Leu | Leu | Arg | Arg | Ala | Asp | Ala | Ile | Phe | Ile | |
| | | | 420 | | | | 425 | | | | 430 | | | | | |
| gag | gaa | ctg | cgt | aaa | gcg | gac | ctg | tac | gac | aaa | gtc | agc | cag | gcg | ttc | 1344 |
| Glu | Glu | Leu | Arg | Lys | Ala | Asp | Leu | Tyr | Asp | Lys | Val | Ser | Gln | Ala | Phe | |
| | | | 435 | | | | 440 | | | | 445 | | | | | |
| act | gtg | ttc | ctg | ccg | ata | cgt | tcc | gtt | ggc | gta | atg | ggc | gat | ggt | cgt | 1392 |
| Thr | Val | Phe | Leu | Pro | Ile | Arg | Ser | Val | Gly | Val | Met | Gly | Asp | Gly | Arg | |
| | 450 | | | | | 455 | | | | | 460 | | | | | |
| aag | tat | gac | tgg | gtt | gtc | tct | ctg | cgt | gct | gtc | gaa | acc | atc | gac | ttt | 1440 |
| Lys | Tyr | Asp | Trp | Val | Val | Ser | Leu | Arg | Ala | Val | Glu | Thr | Ile | Asp | Phe | |
| 465 | | | | | 470 | | | | | 475 | | | | | 480 | |
| atg | acc | gca | cac | tgg | gcg | cat | ctg | ccg | tac | gat | ttc | ctc | ggt | cgc | gtt | 1488 |
| Met | Thr | Ala | His | Trp | Ala | His | Leu | Pro | Tyr | Asp | Phe | Leu | Gly | Arg | Val | |
| | | | | 485 | | | | | 490 | | | | | 495 | | |
| tcc | aac | cgc | att | atc | aat | gaa | gtg | aac | ggt | att | tcc | cgc | gtg | gtg | tat | 1536 |
| Ser | Asn | Arg | Ile | Ile | Asn | Glu | Val | Asn | Gly | Ile | Ser | Arg | Val | Val | Tyr | |
| | | | 500 | | | | 505 | | | | 510 | | | | | |
| gac | atc | agc | ggc | aag | ccg | cca | gct | acc | att | gag | tgg | gaa | tga | | | 1578 |
| Asp | Ile | Ser | Gly | Lys | Pro | Pro | Ala | Thr | Ile | Glu | Trp | Glu | | | | |
| | | | 515 | | | | 520 | | | | 525 | | | | | |

<210> SEQ ID NO 20
<211> LENGTH: 525
<212> TYPE: PRT
<213> ORGANISM: Artificial Sequence
<220> FEATURE:
<223> OTHER INFORMATION: amino acid sequence of F12C

<400> SEQUENCE: 20

Met Thr Glu Asn Ile His Lys His Arg Ile Leu Ile Leu Asp Phe Gly

-continued

```
              1               5                  10                 15
        Ser Gln Tyr Thr Gln Leu Val Ala Arg Val Arg Glu Leu Gly Val
                         20                  25                 30

Tyr Cys Glu Leu Trp Ala Trp Asp Val Thr Glu Ala Gln Ile Arg Asp
                         35                  40                 45

Phe Asn Pro Ser Gly Ile Ile Leu Ser Gly Gly Pro Glu Ser Thr Thr
                         50                  55                 60

Glu Glu Asn Ser Pro Arg Ala Pro Gln Tyr Val Phe Glu Ala Gly Val
        65                   70                  75                 80

Pro Val Phe Gly Val Ala Tyr Gly Met Gln Thr Met Val Met Gln Leu
                             85                  90                 95

Gly Gly His Val Glu Ala Ser Asn Glu Arg Glu Phe Gly Tyr Ala Gln
                             100                 105                110

Val Glu Val Val Asn Asp Ser Ala Leu Val Arg Gly Ile Glu Asp Ala
                             115                 120                125

Leu Thr Ala Asp Gly Lys Pro Leu Leu Asp Val Trp Met Ser His Gly
                             130                 135                140

Asp Lys Val Thr Ala Ile Pro Pro Asp Phe Ile Thr Val Ala Ser Thr
        145                  150                 155                160

Glu Ser Cys Pro Phe Ala Ile Met Ala Asn Glu Glu Lys Arg Phe Tyr
                             165                 170                175

Gly Val Gln Phe His Pro Glu Val Thr His Thr Arg Gln Gly Met Arg
                             180                 185                190

Met Leu Glu Arg Phe Val Arg Asp Ile Cys Gln Cys Glu Ala Leu Trp
                             195                 200                205

Thr Pro Ala Lys Ile Ile Asp Asp Ala Val Ala Arg Ile Arg Glu Gln
                             210                 215                220

Val Gly Asp Asp Lys Val Ile Leu Gly Leu Ser Gly Gly Val Asp Ser
        225                  230                 235                240

Ser Val Thr Ala Met Leu Leu His Arg Ala Ile Gly Lys Asn Leu Thr
                             245                 250                255

Cys Val Phe Val Asp Asn Gly Leu Leu Arg Leu Asn Glu Ala Glu Gln
                             260                 265                270

Val Leu Asp Met Phe Gly Asp His Phe Gly Leu Asn Ile Val His Val
                             275                 280                285

Pro Ala Glu Asp Arg Phe Leu Ser Ala Leu Ala Gly Glu Asn Asp Pro
                             290                 295                300

Glu Ala Lys Arg Lys Ile Ile Gly Arg Val Phe Val Glu Val Phe Asp
        305                  310                 315                320

Glu Glu Ala Leu Lys Leu Glu Asp Val Lys Trp Leu Ala Gln Gly Thr
                             325                 330                335

Ile Tyr Pro Asp Val Ile Glu Ser Ala Ala Ser Ala Thr Gly Lys Ala
                             340                 345                350

His Val Ile Lys Ser His His Asn Val Gly Gly Leu Pro Lys Glu Met
                             355                 360                365

Lys Met Gly Leu Val Glu Pro Leu Lys Glu Leu Phe Lys Asp Glu Val
                             370                 375                380

Arg Lys Ile Gly Leu Glu Leu Gly Leu Pro Tyr Asp Met Leu Tyr Arg
        385                  390                 395                400

His Pro Phe Pro Gly Pro Gly Leu Gly Val Arg Val Leu Gly Glu Val
                             405                 410                415

Lys Lys Glu Tyr Cys Asp Leu Leu Arg Arg Ala Asp Ala Ile Phe Ile
                             420                 425                430
```

-continued

```
Glu Glu Leu Arg Lys Ala Asp Leu Tyr Asp Lys Val Ser Gln Ala Phe
        435                 440                 445
Thr Val Phe Leu Pro Ile Arg Ser Val Gly Val Met Gly Asp Gly Arg
450                 455                 460
Lys Tyr Asp Trp Val Val Ser Leu Arg Ala Val Glu Thr Ile Asp Phe
465                 470                 475                 480
Met Thr Ala His Trp Ala His Leu Pro Tyr Asp Phe Leu Gly Arg Val
                485                 490                 495
Ser Asn Arg Ile Ile Asn Glu Val Asn Gly Ile Ser Arg Val Val Tyr
                500                 505                 510
Asp Ile Ser Gly Lys Pro Pro Ala Thr Ile Glu Trp Glu
        515                 520                 525

<210> SEQ ID NO 21
<211> LENGTH: 1578
<212> TYPE: DNA
<213> ORGANISM: Artificial Sequence
<220> FEATURE:
<223> OTHER INFORMATION: DNA sequence of F63C
<220> FEATURE:
<221> NAME/KEY: CDS
<222> LOCATION: (1)...(1575)
<223> OTHER INFORMATION: amino acid sequence of F63C

<400> SEQUENCE: 21 atg acg gaa aac att cat aag cat cgc atc ctc att ctg gac ttc ggt      48
Met Thr Glu Asn Ile His Lys His Arg Ile Leu Ile Leu Asp Phe Gly
1               5                   10                  15 tct cag tac act caa ctg gtt gcg cgc cgc gtg cgt gag ctg ggt gtt      96
Ser Gln Tyr Thr Gln Leu Val Ala Arg Arg Val Arg Glu Leu Gly Val
            20                  25                  30 tac tgc gaa ctg tgg gcg tgg gat gtg aca gaa gca caa att cgt gac     144
Tyr Cys Glu Leu Trp Ala Trp Asp Val Thr Glu Ala Gln Ile Arg Asp
        35                  40                  45 ttc aat cca agc ggc att att ctt tcc ggc ggc ccg gaa agt act act     192
Phe Asn Pro Ser Gly Ile Ile Leu Ser Gly Gly Pro Glu Ser Thr Thr
    50                  55                  60 gaa gaa aac agt ccg cgt gcg ccg cag tat gtc ttt gaa gca ggc gta     240
Glu Glu Asn Ser Pro Arg Ala Pro Gln Tyr Val Phe Glu Ala Gly Val
65                  70                  75                  80 ccg gta ttc ggc gtt gca tat ggc atg cag acc atg gta atg cag ttg     288
Pro Val Phe Gly Val Ala Tyr Gly Met Gln Thr Met Val Met Gln Leu
                85                  90                  95 ggc ggt cac att gaa gcc tct aac gaa cgt gaa ttt ggc tac gcg cag     336
Gly Gly His Ile Glu Ala Ser Asn Glu Arg Glu Phe Gly Tyr Ala Gln
            100                 105                 110 gct gaa gtc gta aac gac agc gca ctg gtt cgc ggt atc gaa gat gcg     384
Ala Glu Val Val Asn Asp Ser Ala Leu Val Arg Gly Ile Glu Asp Ala
        115                 120                 125 ctg acc gca gac ggt aaa ccg ctg ctc gat gtc tgg atg agc cac ggc     432
Leu Thr Ala Asp Gly Lys Pro Leu Leu Asp Val Trp Met Ser His Gly
    130                 135                 140 gat aaa gtt acc gct att ccg tcc gac ttc atc acc gta gcc agc acc     480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat     528
Glu Ser Cys Pro Phe Ala Ile Met Ala Asn Glu Glu Lys Arg Phe Tyr
                165                 170                 175 ggc gta cag ttc cac ccg gaa gtg act cat acc cgc cag ggt acg cgc     576
Gly Val Gln Phe His Pro Glu Val Thr His Thr Arg Gln Gly Thr Arg
            180                 185                 190
```

```
atg ctg gag cgt ttt gtg cgt gat atc tgc cag tgt gaa gcc ctg tgg      624
Met Leu Glu Arg Phe Val Arg Asp Ile Cys Gln Cys Glu Ala Leu Trp
        195                 200                 205 acg cca gcg aaa att atc gac gat gct gta gct cgc atc cgc gag cag      672
Thr Pro Ala Lys Ile Ile Asp Asp Ala Val Ala Arg Ile Arg Glu Gln
210                 215                 220 gta ggc gac gat aaa gtt atc ctc ggc ctc tct ggt ggt gtg gat tcc      720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act      768
Ser Val Thr Ala Met Leu Leu His Arg Ala Ile Gly Lys Asn Leu Thr
                245                 250                 255 tgc gta ttc gtc gac aac ggc ctg ctg cgc ctc aac gaa gca gag cag      816
Cys Val Phe Val Asp Asn Gly Leu Leu Arg Leu Asn Glu Ala Glu Gln
                260                 265                 270 gtt ctg gat atg ttt ggc gat cac ttt ggt ctt aac att gtt cac gta      864
Val Leu Asp Met Phe Gly Asp His Phe Gly Leu Asn Ile Val His Val
                275                 280                 285 ccg gca gaa gat cgc ttc ctg tca gcg ctg gct ggc gaa aac gat ccg      912
Pro Ala Glu Asp Arg Phe Leu Ser Ala Leu Ala Gly Glu Asn Asp Pro
            290                 295                 300 gaa gca aaa cgt aaa atc atc ggt cgc gtt ttc gtt gaa gta ttc gat      960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc     1008
Glu Glu Ala Leu Lys Leu Glu Asp Val Lys Trp Leu Ala Gln Gly Thr
                325                 330                 335 atc tac cct gac gtt atc gaa tct gcg gcg tct gca acc ggt aaa gca     1056
Ile Tyr Pro Asp Val Ile Glu Ser Ala Ala Ser Ala Thr Gly Lys Ala
                340                 345                 350 cac gtc atc aaa tct cac cac aac gtg ggc ggc ctg ccg aaa gag atg     1104
His Val Ile Lys Ser His His Asn Val Gly Gly Leu Pro Lys Glu Met
            355                 360                 365 aag atg ggc ctg gtt gaa ccg ctg aaa gag ctg ttc aaa gac gaa gtg     1152
Lys Met Gly Leu Val Glu Pro Leu Lys Glu Leu Phe Lys Asp Glu Val
370                 375                 380 cgt aag att ggt ctg gag ctg ggc ctg ccg tac gac atg ctg tac cgt     1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg     1248
His Pro Phe Pro Gly Pro Gly Leu Gly Val Arg Val Leu Gly Glu Val
                405                 410                 415 aag aaa gag tac tgt gac ctg ctg cgc cgt gct gac gcc atc ttc att     1296
Lys Lys Glu Tyr Cys Asp Leu Leu Arg Arg Ala Asp Ala Ile Phe Ile
                420                 425                 430 gaa gaa ctg cgt aaa gcg gac ctg tac gac aaa gtc agc cag gcg ttc     1344
Glu Glu Leu Arg Lys Ala Asp Leu Tyr Asp Lys Val Ser Gln Ala Phe
            435                 440                 445 act gtg ttc ctg ccg ata cgt tcc gtt ggc gta atg ggc gat ggt cgt     1392
Thr Val Phe Leu Pro Ile Arg Ser Val Gly Val Met Gly Asp Gly Arg
            450                 455                 460 aag tat ggc tgg gtt gtc tct ctg cgt gct gtc gaa acc atc gac ttt     1440
Lys Tyr Gly Trp Val Val Ser Leu Arg Ala Val Glu Thr Ile Asp Phe
465                 470                 475                 480 atg acc gca cac tgg gcg cat ctg ccg tac gat ttc ctc ggt cgc gtt     1488
Met Thr Ala His Trp Ala His Leu Pro Tyr Asp Phe Leu Gly Arg Val
                485                 490                 495 tcc aac cgc att atc aat gaa gtg aac ggt att tcc cgc gtg gtg tat     1536
Ser Asn Arg Ile Ile Asn Glu Val Asn Gly Ile Ser Arg Val Val Tyr
            500                 505                 510
```

```
gac atc agc ggc aag ccg cca gct acc att gag tgg gaa tga                    1578
Asp Ile Ser Gly Lys Pro Pro Ala Thr Ile Glu Trp Glu
        515                 520                 525
```

<210> SEQ ID NO 22
<211> LENGTH: 525
<212> TYPE: PRT
<213> ORGANISM: Artificial Sequence
<220> FEATURE:
<223> OTHER INFORMATION: amino acid sequence of F63C

<400> SEQUENCE: 22

```
Met Thr Glu Asn Ile His Lys His Arg Ile Leu Ile Leu Asp Phe Gly
 1               5                  10                  15

Ser Gln Tyr Thr Gln Leu Val Ala Arg Val Arg Glu Leu Gly Val
            20                  25                  30

Tyr Cys Glu Leu Trp Ala Trp Asp Val Thr Glu Ala Gln Ile Arg Asp
        35                  40                  45

Phe Asn Pro Ser Gly Ile Ile Leu Ser Gly Gly Pro Glu Ser Thr Thr
    50                  55                  60

Glu Glu Asn Ser Pro Arg Ala Pro Gln Tyr Val Phe Glu Ala Gly Val
65                  70                  75                  80

Pro Val Phe Gly Val Ala Tyr Gly Met Gln Thr Met Val Met Gln Leu
                85                  90                  95

Gly Gly His Ile Glu Ala Ser Asn Glu Arg Glu Phe Gly Tyr Ala Gln
            100                 105                 110

Ala Glu Val Val Asn Asp Ser Ala Leu Val Arg Gly Ile Glu Asp Ala
        115                 120                 125

Leu Thr Ala Asp Gly Lys Pro Leu Leu Asp Val Trp Met Ser His Gly
    130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Glu Lys Arg Phe Tyr
                165                 170                 175

Gly Val Gln Phe His Pro Glu Val Thr His Thr Arg Gln Gly Thr Arg
            180                 185                 190

Met Leu Glu Arg Phe Val Arg Asp Ile Cys Gln Cys Glu Ala Leu Trp
        195                 200                 205

Thr Pro Ala Lys Ile Ile Asp Asp Ala Val Ala Arg Ile Arg Glu Gln
    210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
        275                 280                 285

Pro Ala Glu Asp Arg Phe Leu Ser Ala Leu Ala Gly Glu Asn Asp Pro
    290                 295                 300

Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
                325                 330                 335

Ile Tyr Pro Asp Val Ile Glu Ser Ala Ala Ser Ala Thr Gly Lys Ala
            340                 345                 350
```

-continued

```
His Val Ile Lys Ser His His Asn Val Gly Gly Leu Pro Lys Glu Met
        355                 360                 365
Lys Met Gly Leu Val Glu Pro Leu Lys Glu Leu Phe Lys Asp Glu Val
    370                 375                 380
Arg Lys Ile Gly Leu Glu Leu Gly Leu Pro Tyr Asp Met Leu Tyr Arg
385                 390                 395                 400
His Pro Phe Pro Gly Pro Gly Leu Gly Val Arg Val Leu Gly Glu Val
            405                 410                 415
Lys Lys Glu Tyr Cys Asp Leu Leu Arg Arg Ala Asp Ala Ile Phe Ile
        420                 425                 430
Glu Glu Leu Arg Lys Ala Asp Leu Tyr Asp Lys Val Ser Gln Ala Phe
            435                 440                 445
Thr Val Phe Leu Pro Ile Arg Ser Val Gly Val Met Gly Asp Gly Arg
    450                 455                 460
Lys Tyr Gly Trp Val Val Ser Leu Arg Ala Val Glu Thr Ile Asp Phe
465                 470                 475                 480
Met Thr Ala His Trp Ala His Leu Pro Tyr Asp Phe Leu Gly Arg Val
            485                 490                 495
Ser Asn Arg Ile Ile Asn Glu Val Asn Gly Ile Ser Arg Val Val Tyr
        500                 505                 510
Asp Ile Ser Gly Lys Pro Pro Ala Thr Ile Glu Trp Glu
        515                 520                 525
```

<210> SEQ ID NO 23
<211> LENGTH: 29
<212> TYPE: DNA
<213> ORGANISM: Artificial Sequence
<220> FEATURE:
<223> OTHER INFORMATION: primer for mutagenesis of guaA

<400> SEQUENCE: 23
cgcgaattca tgacggaaaa cattcataa                                   29

<210> SEQ ID NO 24
<211> LENGTH: 28
<212> TYPE: DNA
<213> ORGANISM: Artificial Sequence
<220> FEATURE:
<223> OTHER INFORMATION: primer for mutagenesis of guaA

<400> SEQUENCE: 24
ctagtctaga tcattcccac tcaatggt                                    28

<210> SEQ ID NO 25
<211> LENGTH: 32
<212> TYPE: DNA
<213> ORGANISM: Artificial Sequence
<220> FEATURE:
<223> OTHER INFORMATION: primer for mutagenesis of guaA

<400> SEQUENCE: 25
acgtgccggc atgacggaaa acattcataa gc                               32

<210> SEQ ID NO 26
<211> LENGTH: 31
<212> TYPE: DNA
<213> ORGANISM: Artificial Sequence
<220> FEATURE:
<223> OTHER INFORMATION: primer for mutagenesis of guaA

<400> SEQUENCE: 26
acgtggatcc tcattcccac tcaatggtag c                                31

```
<210> SEQ ID NO 27
<211> LENGTH: 36
<212> TYPE: DNA
<213> ORGANISM: Artificial Sequence
<220> FEATURE:
<223> OTHER INFORMATION: primer for mutagenesis of guaA

<400> SEQUENCE: 27
ccggtattcg gcgttgcata tggcatgcag accatg                              36

<210> SEQ ID NO 28
<211> LENGTH: 36
<212> TYPE: DNA
<213> ORGANISM: Artificial Sequence
<220> FEATURE:
<223> OTHER INFORMATION: primer for mutagenesis of guaA

<400> SEQUENCE: 28
catggtctgc atgccatatg caacgccgaa taccgg                              36
```